(12) United States Patent
Roessler et al.

(10) Patent No.: US 6,552,245 B1
(45) Date of Patent: Apr. 22, 2003

(54) ABSORBENT ARTICLE HAVING AN EXTENSIBLE OUTER COVER AND AN EXTENSIBLE BODYSIDE LINER

(75) Inventors: Thomas Harold Roessler, Menasha, WI (US); Paul Joseph Datta, Appleton, WI (US); Mark George Everson, Neenah, WI (US); Yung Hsiang Huang, Appleton, WI (US); Gary Lee Travis, Oshkosh, WI (US); Duane Girard Uitenbroek, Little Chute, WI (US); Paul Theodore VanGompel, Hortonville, WI (US); Michael Tod Morman, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/563,417

(22) Filed: May 3, 2000

(51) Int. Cl.[7] .................................................. A61F 13/15
(52) U.S. Cl. .................. 604/367; 604/370; 604/385.22
(58) Field of Search ....................... 604/385.01, 385.22, 604/385.23, 367, 378, 384, 370

(56) References Cited

U.S. PATENT DOCUMENTS

| | | | |
|---|---|---|---|
| 4,655,760 A | 4/1987 | Morman et al. | |
| 4,661,102 A | 4/1987 | Shikata et al. | |
| 4,662,877 A | 5/1987 | Williams | |
| 4,663,220 A | 5/1987 | Wisneski et al. | |
| 4,699,620 A | 10/1987 | Bernardin | |

(List continued on next page.)

FOREIGN PATENT DOCUMENTS

| | | |
|---|---|---|
| EP | 0 217 032 A2 | 4/1987 |
| EP | 0567792 B1 | 1/1998 |
| EP | 0804132 B1 | 6/1999 |
| WO | WO 95/16425 A2 | 6/1995 |
| WO | WO 96/22064 A1 | 7/1996 |
| WO | WO 99/33424 A1 | 7/1999 |
| WO | WO 99/33425 A1 | 7/1999 |
| WO | WO 00/30584 A1 | 6/2000 |
| WO | WO 00/38911 A1 | 7/2000 |
| WO | WO 00/38913 A1 | 7/2000 |
| WO | WO 01/43969 A1 | 6/2001 |
| WO | WO 01/82849 A1 | 11/2001 |
| WO | WO 01/82850 A1 | 11/2001 |
| WO | WO 01/82851 A1 | 11/2001 |
| WO | WO 01/82852 A1 | 11/2001 |

OTHER PUBLICATIONS

American Society for Testing Materials (ASTM) Designation: D882–95a, "Standard Test Method For Tensile Properties of Thin Plastic Sheeting[1]", pp. 182–187, published Dec. 1995.

Federal Test Method Std. (FTMS) No. 191A, Method 5514, "Water Resistance of Cloth; Low Range, Hydrostatic Pressure Method", dated Jul. 20, 1978.

Association of the Nonwoven Fabric Industry (INDA) Standard Test: IST 70.4(99) "Standard Test Method for Water Vapor Transmission Rate through Non Woven and Plastic Film Using a Guard Film and Vapor Pressure Sensor", published 1999.

*Primary Examiner*—Aaron J. Lewis
*Assistant Examiner*—Jacqueline F Stephens
(74) *Attorney, Agent, or Firm*—Jeffrey B. Curtin; Alyssa A. Dudkowski

(57) ABSTRACT

A disposable absorbent article is provided which includes a substantially liquid-impermeable, extensible outer cover, a liquid permeable, extensible bodyside liner, and an absorbent body located between the outer cover and the bodyside liner. The extensible outer cover and extensible bodyside liner can be configured to provide a substantially permanent deformation of at least about 10 percent when subjected to a tensile force of 100 gmf per inch (per 2.54 cm) of width according to the Material Elongation and Deformation Tensile Test set forth herein.

30 Claims, 6 Drawing Sheets

U.S. PATENT DOCUMENTS

| | | |
|---|---|---|
| 4,701,171 A | 10/1987 | Boland et al. |
| 4,701,174 A | 10/1987 | Johnson |
| 4,704,114 A | 11/1987 | Wilson et al. |
| 4,704,116 A | 11/1987 | Enloe |
| 4,710,187 A | 12/1987 | Boland et al. |
| 4,756,709 A | 7/1988 | Stevens |
| 4,777,073 A | 10/1988 | Sheth |
| 4,798,603 A | 1/1989 | Meyer et al. |
| 4,834,738 A | 5/1989 | Kielpikowski et al. |
| 4,872,871 A | 10/1989 | Proxmire et al. |
| 4,892,598 A | 1/1990 | Stevens et al. |
| 4,941,933 A | 7/1990 | Korpman |
| 4,949,668 A | 8/1990 | Heindel et al. |
| 4,965,122 A | 10/1990 | Morman |
| 4,983,109 A | 1/1991 | Miller et al. |
| 5,114,781 A | 5/1992 | Morman |
| 5,116,662 A | 5/1992 | Morman |
| 5,176,668 A | 1/1993 | Bernardin |
| 5,176,672 A | 1/1993 | Bruemmer et al. |
| 5,192,606 A | 3/1993 | Proxmire et al. |
| 5,226,992 A * | 7/1993 | Morman .................... 156/62.4 |
| 5,269,775 A | 12/1993 | Freeland et al. |
| 5,360,422 A | 11/1994 | Brownlee et al. |
| 5,399,219 A | 3/1995 | Roessler et al. |
| 5,472,518 A * | 12/1995 | Patnode et al. .............. 134/34 |
| 5,486,166 A | 1/1996 | Bishop et al. |
| 5,490,846 A | 2/1996 | Ellis et al. |
| 5,496,295 A * | 3/1996 | Wilfong et al. ............. 604/332 |
| 5,496,298 A | 3/1996 | Kuepper et al. |
| 5,509,915 A | 4/1996 | Hanson et al. |
| 5,527,303 A | 6/1996 | Milby, Jr. et al. |
| 5,540,796 A | 7/1996 | Fries |
| 5,554,143 A | 9/1996 | Roe et al. |
| 5,554,145 A | 9/1996 | Roe et al. |
| 5,569,232 A | 10/1996 | Roe et al. |
| 5,575,782 A | 11/1996 | Hasse et al. |
| 5,595,618 A | 1/1997 | Fries et al. |
| 5,611,791 A * | 3/1997 | Gorman et al. ............. 604/391 |
| 5,624,424 A | 4/1997 | Saisaka et al. |
| 5,650,223 A | 7/1997 | Weinberger et al. |
| 5,728,219 A | 3/1998 | Allen et al. |
| 5,730,919 A * | 3/1998 | Wilfong et al. ........ 264/173.11 |
| 5,807,368 A | 9/1998 | Helmer |
| 5,807,371 A | 9/1998 | Toyoda et al. |
| 5,824,004 A | 10/1998 | Osborn, III et al. |
| 5,846,232 A | 12/1998 | Serbiak et al. |
| 5,865,824 A | 2/1999 | Chen et al. |
| 5,883,028 A | 3/1999 | Morman et al. |
| 6,028,240 A * | 2/2000 | Wessel et al. ............... 604/358 |
| 6,036,805 A | 3/2000 | McNichols |
| 6,049,023 A | 4/2000 | Blenke et al. |
| 6,096,017 A | 8/2000 | Osborn, III |
| 6,245,401 B1 * | 6/2001 | Ying et al. .................... 428/58 |
| 6,264,641 B1 | 7/2001 | Van Gompel et al. |
| 6,264,864 B1 * | 7/2001 | MacKay .................... 264/154 |
| 6,287,287 B1 | 9/2001 | Elsberg |
| 6,316,687 B1 | 11/2001 | Davis et al. |

\* cited by examiner

ABSORBENT ARTICLE HAVING AN EXTENSIBLE OUTER COVER AND AN EXTENSIBLE BODYSIDE LINER

FIELD OF THE INVENTION

The present invention relates to absorbent articles, desirably disposable absorbent articles, which have a distinctive extensible outer cover and bodyside liner that provide improved fit in use.

BACKGROUND OF THE INVENTION

It is desired that absorbent articles such as diapers, training pants or incontinence garments provide a close, comfortable fit about the wearer and contain body exudates while maintaining skin health. In certain circumstances, it is also desirable that such absorbent articles are capable of being pulled up or down over the hips of the wearer to allow the wearer or caregiver to easily pull the article on and easily remove the article if it has not been soiled. For example, such absorbent articles can assist in the toilet training of children.

Many conventional absorbent articles have typically employed fasteners that attach the waist sections of the articles around a wearer as well as various configurations of waist elastics, leg elastics, elasticized liners, and elasticized outer covers. The fasteners and elastic components have been employed to help produce and maintain the fit of the articles about the body contours of the wearer that can lead to improved containment. Maintaining this fit as the wearer moves and changes body position has been particularly difficult. For example, articles such as diapers are typically applied while the wearer is in a prone position wherein their torso is extended and their abdomen is sunken. As the wearer changes from the prone position to a sitting position, the wearer's torso compresses and their abdomen extends outwardly thereby exerting forces on the article. If the waistband of the article does not have enough "give", such forces can cause the waistband to shift that can undesirably result in increased leakage.

In an attempt to provide a maintained fit during movement, some conventional absorbent articles have included an outer cover composed of elastomeric materials, such as elastomeric, stretch-bonded-laminate materials. Such materials have included a layer of meltblown elastomeric fibers which has been stretched and sandwiched between facing layers composed of polypropylene spunbond nonwoven materials. The meltblown layer has typically been pattern-bonded to the facing layers with thermal bonds, sonic bonds and/or adhesive bonds. Other conventional absorbent articles have included folded pleats in the outer cover. The pleats are arranged to expand open as the article absorbs liquids.

In absorbent articles that are capable of being pulled up or down over the hips of the wearer, the ability of the article to provide and maintain the desired fit is particularly important. For example, some conventional absorbent articles, such as conventional training pants, have included integral side panels that connect the front waist section to the back waist section of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled but typically are not refastenable.

Moreover, in an attempt to reduce the humidity level within such absorbent articles to help maintain the health of the wearer's skin, breathable polymer films have been employed as outer covers for such absorbent articles. The breathable films are typically constructed with micropores to provide desired levels of liquid impermeability and air permeability. Other absorbent article designs have been arranged to provide breathable regions in the form of breathable panels or perforated regions in otherwise vapor-impermeable outer covers to help ventilate the articles.

However, many of such attempts to provide absorbent articles that provide the desired fit while maintaining breathability have not been completely satisfactory. For example, some absorbent articles that include elastic outer cover materials have resulted in excessive skin irritation as it has been difficult to control the tension in such products. Moreover, such elastic outer covers typically have not exhibited the desired resistance to leakage as they have not readily expanded to provide void volume for the containment of fecal exudates. In addition, absorbent articles such as training pants have not always been able to achieve a close conforming fit to the wearer while still being able to expand enough to be pulled up and down over the hips of the wearer. Often such training pants fit the waist of the wearer loosely, which can undesirably result in leaks. As a result, many of such articles have not contained bodily exudates as effectively as conventional diaper-type articles which can be adjusted to achieve a more conforming fit to the wearer.

Further, articles which employ selectively located breathable panels can be difficult to manufacture. In addition, articles that employ microporous or perforated films that are highly breathable over their entire surface can exhibit excessive leakage of liquids or high levels of moisture or dampness on their outer surface in the region of the article receiving the greatest insults. As a result, the breathability of such microporous and perforated films has been maintained at relatively low levels to reduce the incidence of leakage and dampness on the outer cover. Thus, many of such absorbent articles have not been able to maintain a high level of breathability to sufficiently reduce the hydration of the wearer's skin. As a result, the wearer's skin has remained susceptible to rashes, abrasion and irritation.

Accordingly, despite the attempts to develop improved absorbent articles, there remains a need for absorbent articles that can provide improved fit, resistance to leakage and breathability without excessive irritation to the skin of the wearer. Moreover, in some circumstances, there remains a need that such absorbent articles provide the benefits of conventional training pants and conventional diapers. That is, there remains a need for absorbent articles that conform to the wearer to effectively contain bodily exudates, are breathable and are capable of being pulled up and down over the hips and buttocks of the wearer.

BRIEF DESCRIPTION OF THE INVENTION

In response to the difficulties and problems discussed above, new absorbent article designs have been discovered which provide improved breathability, fit and containment. Generally stated, the present invention provides a disposable absorbent article that defines a front waist section, a rear waist section, an intermediate section which extends between and connects the waist sections, a pair of laterally opposed side edges, a pair of longitudinally opposed waist edges, a longitudinal direction and a lateral direction. The absorbent article includes a substantially liquid-impermeable outer cover, a liquid-permeable bodyside liner and an absorbent body located between the outer cover and the bodyside liner. The absorbent article may also include a pair of fasteners located on the laterally opposed side edges intone of the waist sections. In certain aspects, the disposable absorbent article may be provided in a prefastened, pant-like configuration such that the article can be pulled on or off over the hips of the wearer similar to conventional training pants. For example, the fasteners may refastenably attach the laterally opposed side edges in the front waist section to the laterally opposed side edges in the rear waist section to provide the pant-like, prefastened absorbent article prior to packaging the articles.

In particular aspects, the outer cover may be extensible and configured to provide a substantially permanent deformation of at least about 10 percent, desirably at least about 15 percent, particularly at least about 17 percent, more desirably at least about 20 percent, even more desirably at least about 25 percent, and yet even more desirably at least about 30 percent when subjected to a tensile force of 100 gmf per inch of width according to the Material Elongation and Deformation Tensile Test set forth herein.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

Figure 1:
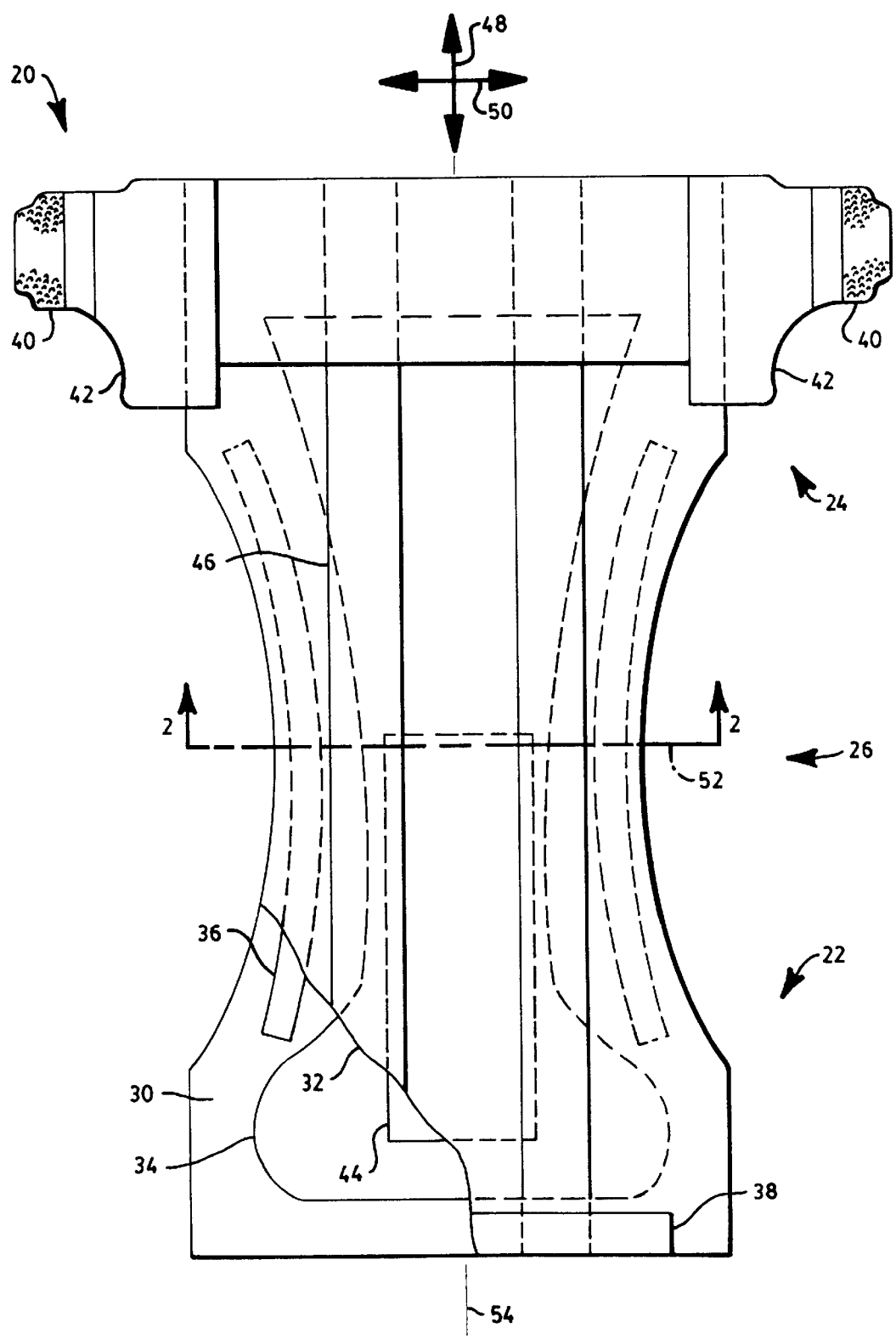
FIG. 1 representatively shows a partially cut-away, top plan view of the inward surface of an example of an article of the invention.

The various aspects and embodiments of the invention will be described in the context of disposable absorbent articles, such as a disposable diaper or training pant. It is, however, readily apparent that the present invention could also be employed with other absorbent articles, such as feminine care articles, incontinence garments and the like. Typically, the disposable articles are intended for limited use and are not intended to be laundered or otherwise cleaned for reuse. A disposable diaper, for example, is discarded after it has become soiled by the wearer.

By incorporating its various aspects, the articles of the present invention can provide improved fit and improved resistance to leakage. In particular, the extensible outer cover of the articles is capable of adjusting to the wearer's movements and the wearer's body position and dimensions for improved performance. In addition, the articles of the invention can provide improved breathability, greater softness, greater coverage over the hips and buttocks of the wearer and more cloth-like properties. Moreover, in certain aspects, the present invention can advantageously provide pant-like, prefastened, absorbent articles that are capable of being reliably pulled up or down over the hips of the wearer to assist in the toilet training of the wearer similar to conventional training pants.

When employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Accordingly, such terms are intended to be synonymous with the words "has", "have", "having", "includes", "including" and any derivatives of these words.

As used herein, the term "extensible material" refers to a material that can a provide a substantially permanent deformation of at least about 10 percent, desirably at least about 15 percent, particularly at least about 17 percent, more desirably at least about 20 percent, even more desirably at least about 25 percent, and yet even more desirably at least about 30 percent when subjected to a tensile force of 100 gmf per inch (per 2.54 cm) of width according to the Material Elongation and Deformation Tensile Test set forth herein. In general, the Material Elongation and Deformation Tensile Test is conducted similar to ASTM Standard Test Method D882 (Tensile Method for Tensile Properties of Thin Plastic Sheeting) dated December 1995. The initial separation of the jaws of the tensile tester is 3 inches (76.2 mm) at a tensile force of about 1 gram force per inch of width of the test sample, and the moving jaw is moved at a constant rate of 127 mm/min. The moving jaw is stopped at an extension where the tensile force equals 1.00 grams force per inch of width of the test sample, held at that extension for a period of 2 minutes, and then returned back to its initial tensile force of about 1 gram force per inch of width of the test sample at a rate of 127 mm/min.

Figure 2:
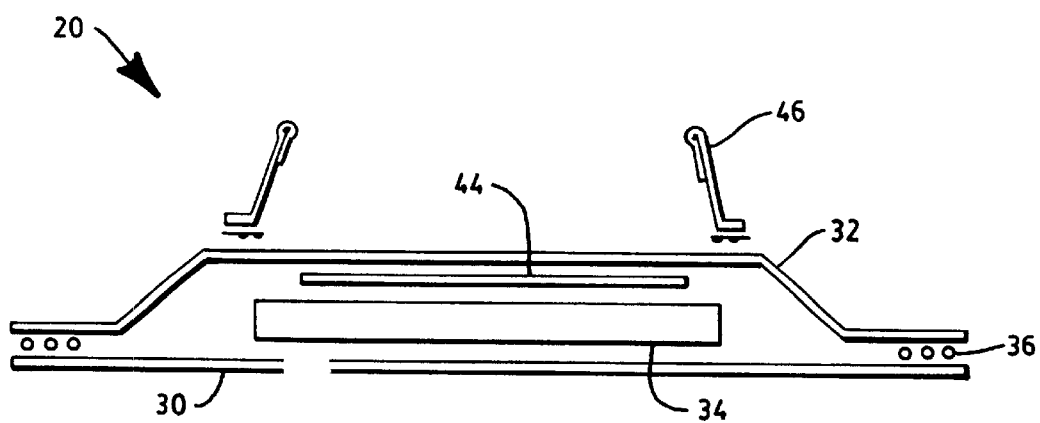
FIG. 2 representatively shows an expanded, lateral cross-sectional view taken with respect to line 2—2 of FIG. 1.

FIG. 1 is a representative plan view of an absorbent article, such as disposable diaper 20, of the present invention in its flat-out, uncontracted state (i.e., with all elastic induced gathering and contraction removed). Portions of the structure are partially cut away to more clearly show the interior construction of diaper 20, and the surface of the diaper which contacts the wearer is facing the viewer. FIG. 2 representatively shows a sectional view of the absorbent article of FIG. 1 taken along line 2—2. With reference to FIGS. 1 and 2, the disposable diaper 20 generally defines a front waist section 22, a rear waist section 24, and an intermediate section 26 which interconnects the front and rear waist sections. The front and rear waist sections 22 and 24 include the general portions of the article which are constructed to extend substantially over the wearer's front and rear abdominal regions, respectively, during use. The intermediate section 26 of the article includes the general portion of the article that is constructed to extend through the wearer's crotch region between the legs. Thus, the intermediate section 26 is an area where repeated liquid surges typically occur in the diaper or other disposable absorbent article.

The absorbent article includes an outer cover 30, a liquid permeable bodyside liner 32 positioned in facing relation with the outer cover 30, and an absorbent body 34, such as an absorbent pad, which is located between the outer cover 30 and the bodyside liner 32. The outer cover 30 defines a length and a width which, in the illustrated embodiment, coincide with the length and width of the diaper 20. The absorbent body 34 generally defines a length and width that are less than the length and width of the outer cover 30, respectively. Thus, marginal portions of the diaper 20, such as marginal sections of the outer cover 30, may extend past the terminal edges of the absorbent body 34. In the illustrated embodiments, for example, the outer cover 30 extends outwardly beyond the terminal marginal edges of the absorbent body 34 to form side margins and end margins of the diaper 20. The bodyside liner 32 is generally coextensive with the outer cover 30 but may optionally cover an area which is larger or smaller than the area of the outer cover 30, as desired. The outer cover 30 and bodyside liner 32 are intended to face the garment and body of the wearer, respectively, while in use.

To provide improved fit and to help reduce leakage of body exudates from the diaper 20, the diaper side margins and end margins may be elasticized with suitable elastic members, such as single or multiple strands of elastic. For example, as representatively illustrated in FIGS. 1 and 2, the diaper 20 may include leg elastics 36 which are constructed to operably gather and shirr the side margins of the diaper 20 to provide elasticized leg bands which can closely fit around the legs of the wearer to reduce leakage and provide improved comfort and appearance. Similarly, waist elastics, 38 can be employed to elasticize the end margins of the diaper 20 to provide elasticized waistbands.

The waist elastics are configured to operably gather and shirr the end margins to provide a resilient, comfortably close fit around the waist of the wearer. In the illustrated embodiments, the elastic members are illustrated in their uncontracted, stretched condition for the purpose of clarity.

Materials suitable for use as the leg elastics 36 and waist elastics 38 are well known to those skilled in the art. Exemplary of such materials are sheets or strands or ribbons of a polymeric, elastomeric material which are adhered to the outer cover 30 in a stretched position, or which are attached to the outer cover 30 while the outer cover is pleated, such that elastic constrictive forces are imparted to the outer cover 30. The leg elastics may also include such materials as polyurethane, synthetic and natural rubber that may optionally be heat shrinkable or heat elasticizable.

Fastening means, such as hook and loop fasteners 40, may be employed to secure the diaper on a wearer. Alteratively, other fastening means, such as buttons, pins, snaps, adhesive tape fasteners, cohesives, mushroom-and-loop fasteners, or the like, may be employed. In the illustrated embodiment, the diaper 20 further includes a pair of side panels 42 to which the fasteners 40 are attached. Generally, the side panels 42 are attached to the side edges of the diaper 20 in one of the waist sections and extend laterally outward therefrom. The side panels 42 may be elasticized or otherwise rendered elastomeric.

For example, the side panels 42 may be an elastomeric material such as a neck-bonded laminate (NBL) or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. Examples of articles that include elasticized side panels and selectively configured fastener tabs are described in PCT Patent Application No. WO 95/16425 published Jun. 22, 1995 to Roessler; U.S. Pat. No. 5,399,219 issued Mar. 21, 1995 to Roessler et al.; U.S. Pat. No. 5,540,796 to Fries; and U.S. Pat. No. 5,595,618 to Fries; the disclosures of which are also incorporated herein by reference.

The diaper 20 may also include a surge management layer 44 located between the bodyside liner 32 and the absorbent body 34 to prevent pooling of the fluid exudates and further improve the distribution of the fluid exudates within the diaper 20. The diaper 20 may further include a ventilation layer (not illustrated) located between the absorbent body 34 and the outer cover 30 to insulate the outer cover 30 from the absorbent body 34 to reduce the dampness of the garment facing surface of the outer cover 30. Examples of suitable surge management layers 44 are described in U.S. Pat. No. 5,486,166 to Bishop and U.S. Pat. No. 5,490,846 to Ellis, the entire disclosures of which are hereby incorporated by reference.

As representatively illustrated in FIGS. 1 and 2, the disposable diaper 20 may also include a pair of containment flaps 46 which are configured to provide a barrier to the lateral flow of body exudates. The containment flaps 46 may be located along the laterally opposed side edges of the diaper 20 adjacent the side edges of the absorbent body 34. Each containment flap 46 typically defines an unattached edge which is configured to maintain an upright, perpendicular configuration in at least the intermediate section 26 of the diaper 20 to form a seal against the wearer's body. The containment flaps 46 may extend longitudinally along the entire length of the absorbent body 34 or may only extend partially along the length of the absorbent body 34. When the containment flaps 46 are shorter in length than the absorbent body 34, the containment flaps 46 can be selectively positioned anywhere along the side edges of the diaper 20 in the intermediate section 26. In a particular aspect of the invention, the containment flaps 46 extend along the entire length of the absorbent body 34 to better contain the body exudates.

Such containment flaps 46 are generally well known to those skilled in the art. For example, suitable constructions and arrangements for containment flaps 46 are described in U.S. Pat. No. 4,704,96 issued Nov. 3, 1987, to K. Enloe, the disclosure of which is hereby incorporated by reference.

The diaper 20 may be of various suitable shapes. For example, the diaper may have an overall rectangular shape, T-shape or an approximately hour-glass shape. In the shown embodiment, the diaper 20 has a generally l-shape. The diaper 20 further defines a longitudinal direction 48, a lateral direction 50, a longitudinal centerline 54 and a lateral centerline 52. Other suitable components which may be incorporated on absorbent articles of the present invention include waist flaps and the like which are generally known to those skilled in the art.

Examples of diaper configurations suitable for use in connection with the instant invention which may include other components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are herein incorporated by reference.

The various components of the diaper 20 are integrally assembled together employing various types of suitable attachment means, such as adhesive, sonic bonds, thermal bonds or combinations thereof. In the shown embodiment, for example, the bodyside liner 32 and outer cover 30 may be assembled to each other and to the absorbent body 34 with lines of adhesive, such as a hot melt, pressure-sensitive adhesive. Similarly, other diaper components, such as the elastic members 36 and 38, fastening members 40, and surge layer 44 may be assembled into the article by employing the above-identified attachment mechanisms.

The article of the invention includes a distinctive extensible outer cover 30 which includes an extensible fabric layer which is operatively attached or otherwise joined to extend over a major portion of the outward surface of the article. In regions where the extensible outer cover 30 is not affixed to non-extensible portions of the article or otherwise restricted from extending, the extensible outer cover 30 can be free to advantageously expand with minimal force and with a high amount of permanent deformation. In desired aspects, the outer cover 30 can be extensible along the longitudinal direction 48, lateral direction 50, or along a combination of both the lateral and longitudinal directions.

In particular, it is desirable that the portion of the extensible outer cover 30 located in the waist sections 22 and 24 is capable of extending and permanently deforming in the lateral direction 50 to provide improved fastening of the article about the wearer, improved coverage of the hips and buttocks of the wearer particularly in the rear waist section and enhanced breathability in the waist sections. For example, if the fasteners 40 and or side panels 42 are located along the side edges in the rear waist section 24 of the diaper 20, at least a portion of the outer cover 30 in the rear waist section 24 will desirably extend to provide enhanced coverage over the buttocks of the wearer in use for improved containment and aesthetics. The enhanced buttock coverage is due to the permanent deformation of the outer cover 30 in the rear waist section 24 when lateral forces are exerted to fasten the diaper 20 about the wearer.

Moreover, it is also desirable that at least portions of the extensible outer cover 30 located over the absorbent body 34 can extend during use for improved containment. For example, as the absorbent body 34 absorbs fluid exudates and expands outwardly, the extensible outer cover 30 can readily elongate and extend in correspondence with the expansion of the absorbent body 34 and/or other components of the article to provide void volume to more effectively contain the exudates.

The extensible outer cover 30 may also be selectively elasticized in certain regions by attaching elastomeric components to the extensible outer cover 30 in such regions. For example, the extensible outer cover 30 may be elasticized adjacent the leg openings by attaching the leg elastics 36 to the extensible outer cover 30. Moreover, if desired, substantially non-extensible regions can be created in the extensible outer cover 30 by attaching such regions to a substantially non-extensible component. For example, as described below, the diaper 20 may include an attachment panel attached to the extensible outer cover 30 in the front waist section 22 of the diaper 20. If the attachment panel is made of a non-extensible material it will limit the extensibility of the outer cover 30 in the region it is attached. Generally, it is desirable that the majority of the extensible outer cover 30 remains extensible in use for improved performance.

The extensible outer cover 30 of the present invention is desirably capable of providing a selected elongation when subjected to an applied tensile force. The extensible outer cover 30 is also desirably capable of providing a selected, sustained deformation when subjected to an applied tensile force and then allowed to relax for a selected time period after removing the applied tensile force. The measurement of the selected time period begins immediately after the removal of the tensile force. Desirably, the sustained deformation is a substantially permanent deformation. The selected elongation and sustained deformation can occur at least along the lateral direction 50 of the article.

Optionally, the selected elongation and sustained deformation can occur along the longitudinal direction 48 of the article, or may occur along both the lateral direction and longitudinal direction of the article.

In particular aspects, the extensible outer cover 30 can provide an elongation of at least about 10 percent, desirably at least about 20 percent, more desirably at least about 30 percent and even more desirably at least about 40 percent when subjected to a tensile force of 100 gmf per inch (per 2.54 cm) of width of the test sample according to the Material Elongation and Deformation Tensile Test set forth herein. Elongation less than those above may not provide the desired expansion for the improved fastening, containment, enhanced buttock coverage and breathability discussed herein. In other aspects, the extensible outer cover 30 can be capable of providing an elongation of from about 10 percent to about 200 percent and desirably from about 30 percent to about 100 percent when subjected to a tensile force of 100 gmf per inch (per 2.54 cm) of width of the test sample according to the Material Elongation and Deformation Tensile Test set forth herein.

In certain aspects, the extensible outer cover 30 can also provide a substantially permanent deformation of at least about 10 percent, desirably at least 15 percent, particularly at least about 17 percent, more desirably at least about 20 percent, even more desirably at least about 25 percent and yet even more desirably at least about 30 percent when subjected to a tensile force of 100 gmf per inch (per 2.54 cm) of width of the test sample according to the Material Elongation and Deformation Tensile Test set forth herein. Substantially permanent deformations less than those set forth above may not provide the desired improved fastening, containment, enhanced buttock coverage and breathability. In still other aspects, the extensible outer cover 30 can provide a substantially permanent deformation of from about 10 to about 200 percent and desirably from about 17 to about 100 percent when subjected to the tensile force of 100 gmf per inch (per 2.54 cm) of width of the test sample according to the Material Elongation and Deformation Tensile Test set forth herein.

In particular aspects, the extensible outer cover 30 can provide a combination of elongation and substantially permanent deformation as set forth above for improved performance.

It should be noted that the elongation, extension or permanent deformation properties of the extensible outer cover 30 are determined When the outer cover 30 is dry. Additionally, the percentage of elongation, extension or permanent deformation can be determined in accordance with the following formula:

$$100*(L-L_o)/(L_o);$$

where:

L = either a) extended length for elongation or extension or b) post extended length for set or deformation, and $L_o$ = initial length.

The extension and permanent set or deformation of the extensible outer cover 30 of the different aspects of the present invention is particularly important when the article is provided in a pant-like configuration such as a conventional training pant or prefastened diaper that can be pulled up or down over the hips of the wearer in use. For example, as representatively illustrated in FIG. 5, the diaper 20 may be provided in a prefastened pant-like configuration prior to packaging by releasably engaging the fasteners 40 with the opposite waist section during the manufacturing process. In such a configuration, the diaper 20 and, in particular, the waist sections 22 and 24 of the diaper 20 must be capable of extending such that the diaper 20 can be pulled on over the hips of the wearer. The use of the extensible outer cover 30 as described herein can provide the necessary levels of extensibility to allow the diaper 20 to function in a prefastened configuration.

For example, in embodiments wherein the article is provided in a prefastened, pant-like configuration, the extensible outer cover 30 desirably provides an elongation of at least about 20 percent, more desirably at least about 30 percent and a substantially permanent deformation of at least about 17 percent, more desirably at least about 20 percent when subjected to the tensile force of 100 gmf per inch (per 2.54 cm) of width of the test sample according to the Material Elongation and Deformation Tensile Test set forth herein.

Figure 5:
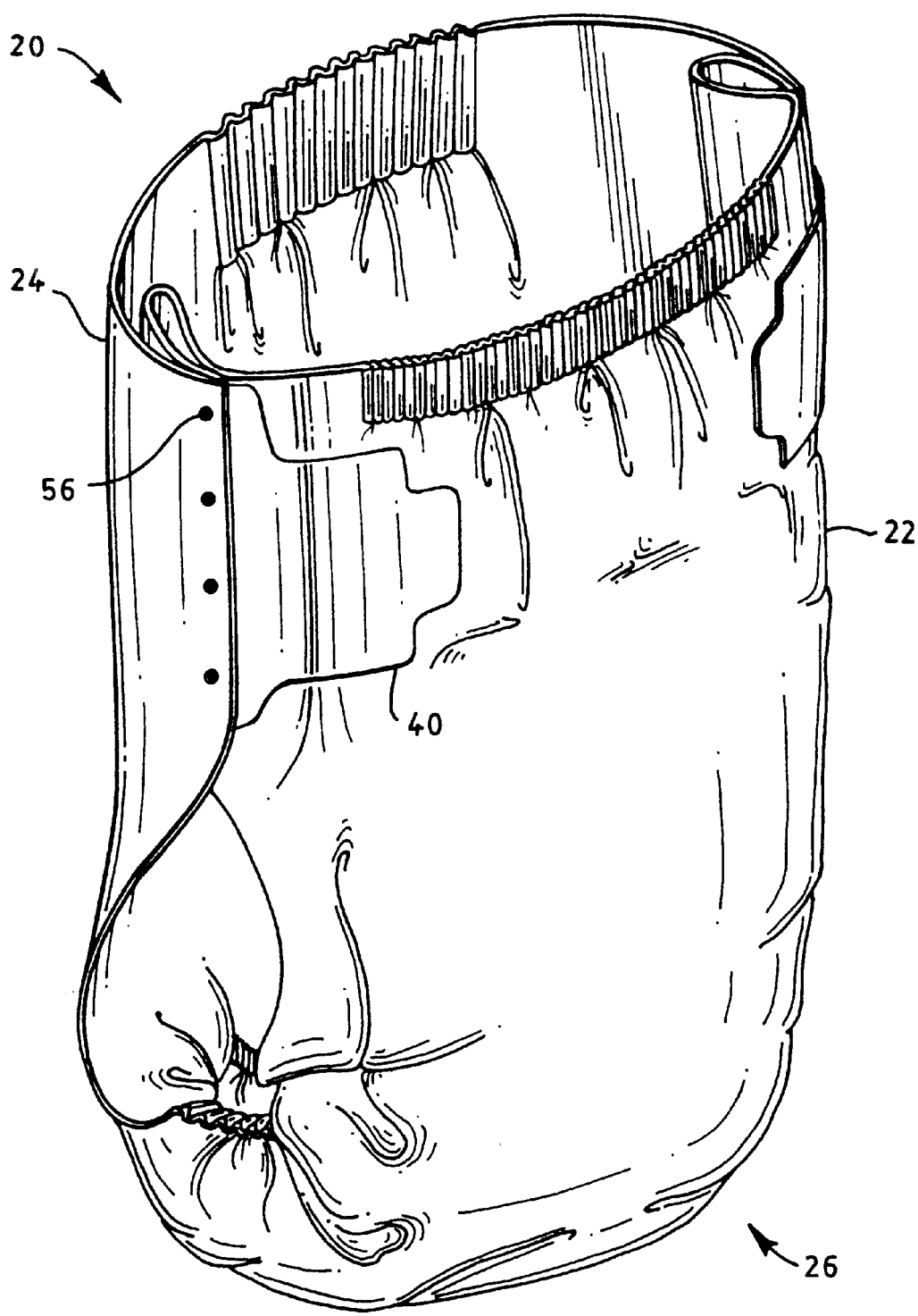
FIG. 5 representatively shows a perspective view of an example of an article of the invention in a prefastened, pant-like configuration.

As illustrated in FIG. 5, the pant-like diaper 20 may include passive bonds 56 between the respective waist sections to assist the fasteners 40 in maintaining the diaper 20 in the prefastened configuration. Absorbent articles including such passive bonds and methods of making them are further described in U.S. patent application entitled "DISPOSABLE ABSORBENT ARTICLES HAVING PASSIVE SIDE BONDS AND ADJUSTABLE FASTENING SYSTEMS" filed in the name of Elsberg on Jun. 19, 1998 and assigned U.S. Ser. No. 09/100,574, and U.S. patent application entitled "METHOD OF MAKING AN ABSORBENT ARTICLE WITH PREFASTENED SIDE PANELS AND ABSORBENT ARTICLES MADE BY THE SAME" filed in the name of McNichols on Jun. 19, 1998 and assigned U.S. Ser. No. 09/100,825, the disclosures of which are hereby incorporated by reference.

The extensible outer cover 30 of the different aspects of the present invention or at least a portion thereof is desirably substantially vapor permeable or breathable to allow the transmission of vapors out of the article to effectively reduce the humidity level within the diaper 20. The vapor permeability of the extensible outer cover 30 is configured to enhance the breathability of the absorbent article to reduce the hydration of the wearer's skin during use without allowing excessive condensation of vapor, such as water, on the garment facing surface of the outer cover 30 which can undesirably dampen the wearer's clothes.

Desirably, the extensible outer cover 30 is constructed to be permeable to at least water vapor. For example, in particular embodiments, the extensible outer cover 30 defines a water vapor transmission rate (WVTR) according to the Mocon Water Vapor Transmission Rate Test set forth herein of at least about 800 g/sq.m/24 hr., desirably at least about 1200 g/sq.m/24 hr, more desirably at least about 2000 g/sq.m/24 hr., and even more desirably at least about 3000 g/sq.m/24 hr. in the non-extended condition. In such embodiments, the extensible outer cover 30 may define a WVTR of from about 800 to about 60,000 g/sq.m/24 hr. Materials which have a WVTR less than those above may not allow a sufficient amount of water vapor diffusion out of the diaper and undesirably result in increased levels of skin hydration.

During use, at least portions of the extensible outer cover 30 may be extended and permanently deformed such that these portions exhibit increased levels of breathability. For example, as representatively illustrated in FIGS. 3 and 4, when the fasteners 40 are extended in the lateral direction 50 when fastening the diaper 20 about the wearer or pulling the diaper on over the hips of the wearer, the forces exerted on the extensible outer cover 30 cause the outer cover 30 to extend and permanently deform at least in portions of the outer cover between the fasteners 40. The permanent deformation or set of the outer cover 30 in the regions between the fasteners increases the level of breathability of the outer cover 30 in such regions. For example, if the fasteners 40 and or side panels 42 are located along the side edges in the rear waist section 24 of the diaper 20, at least a portion of the outer cover 30 in the rear waist section 24 will desirably exhibit an increased level of breathability in use. The enhanced breathability is due to the permanent deformation of the outer cover 30 when lateral forces are exerted to fasten the diaper 20 about the wearer. Thus, in use, the article of the different aspects of the present invention can provide regions or zones that exhibit increased levels of breathability in use.

A suitable method of predicting such levels of increased breathability during use is to measure the breathability of a sample of the outer cover 30 before it is extended and held at an extension of 25 percent. Desirably, the sample of the extensible outer cover 30 of the article of the present invention provides a breathability increase while extended 25 percent of at least about 10 percent, more desirably at least about 25 percent, even more desirably at least about 50 percent, yet even more desirably at least about 100 percent. Breathability increases less than those set forth above may not provide the desired level of enhanced breathability. The breathability of the samples is determined using the Mocon Water Vapor Transmission Rate set forth herein. To ensure the sample is held in the 25% extended condition during the Mocon test, adhesive such as double sided tape commercially available from 3M may be applied to one face of the Mocon sample holder such that the adhesive prevents the sample from retracting.

In a particular embodiment, the extensible outer cover 30 defines a water vapor transmission rate of at least about 800 g/sq.m/24 hr., desirably at least about 1200 g/sq.m/24 hr, more desirably at least about 2000 g/sq.m/24 hr., and even more desirably at least about 3000 g/sq.m/24 hr. in the non-extended condition and a breathability increase as set forth above while it is held at an extension of 25 percent in the lateral direction 50 for improved performance.

Typically, the forces exerted on the outer cover 20 when fastening the diaper 20 about the wearer's waist are localized in at least one of the front and rear waist sections 22 and 24 of the diaper 20. As a result, the extension of the fasteners 40 upon the initial fastening about the wearer tends to cause the outer cover 30 in at least one of the front and rear waist sections 22 and 24 to extend and permanently deform. Such permanent deformation of the outer cover 30 results in increased breathability in at least one of the waist sections 22 and 24 of the diaper 20.

Figure 3:
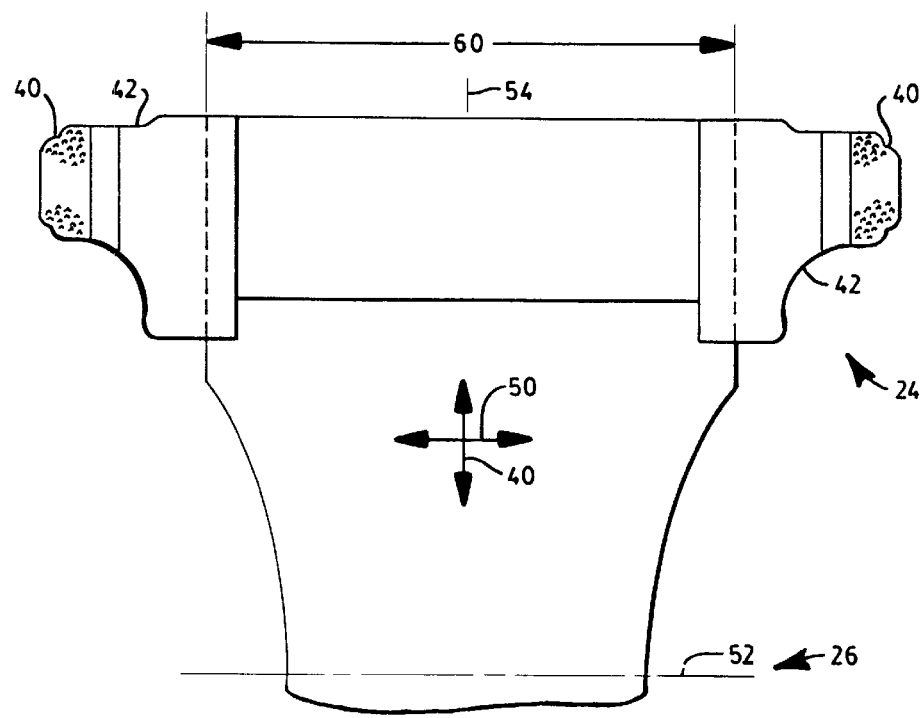
FIG. 3 representatively shows a partial top plan view of the inward surface of the article of FIG. 1 in a relaxed, non-extended configuration.
Figure 4:
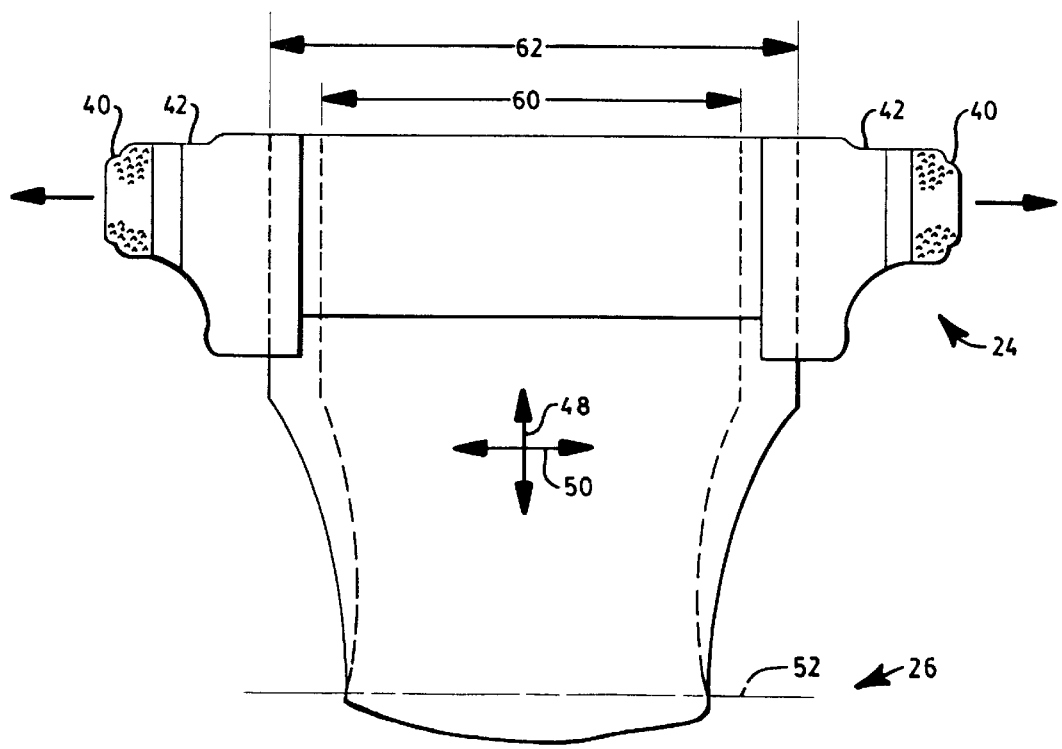
FIG. 4 representatively shows a partial top plan view of the inward surface of the article of FIG. 1 in a relaxed configuration after the fasteners in such article have been subjected to an extension force in the lateral direction thereby permanently extending the outer cover in the waist section of the article.

This increase in breathability of the outer cover 30 in at least one of the waist sections 22 and 24 desirably occurs without a substantial increase in the breathability of the outer cover 30 in the intermediate section 26 of the diaper 20 upon the fastening of the diaper 20 about the wearer. For example, as illustrated in FIGS. 3 and 4, the extensible outer cover 30 may define a non-extended distance 60 between the fasteners 40 prior to use and an extended distance 62 after the fasteners 40 are extended in use to fasten the article about the waist of the wearer. As can be seen in FIG. 4, the extension of the fasteners 40 in the lateral direction 50 extends the outer cover 30 in the rear waist section 24 between the fasteners 40 but does not result in any substantial extension of the outer cover 30 along the lateral centerline 52 of the diaper 20. Thus, in use, the diaper 20 can provide a longitudinal breathability gradient between the waist sections 22 and 24 and the intermediate section 26 of the diaper 20. Such a longitudinal breathability gradient can provide improved water vapor or humidity reduction within the diaper 20 without excessive outer cover dampness and/or leakage since the portion of the diaper intended to receive the majority of the fluid insults, that is the intermediate section 26 of the diaper 20, can exhibit a lower level of breathability than the waist sections 22 and 24 of the diaper 20.

As a result, the extensible outer cover 30 desirably may provide zones of higher breathability in the waist sections 22 or 24 of the diaper 20 in use when compared to the level of breathability of the outer cover 30 in the intermediate section 26 of the diaper 20. The portion of the absorbent 34 located in the waist sections and, in particular, the rear waist section typically stays drier than other portions of the absorbent in use. Thus, in use, the drier absorbent in at least the rear waist section allows a channel for the water vapor adjacent the skin to leave the diaper through the zones of higher breathability in the waist sections thereby leading, directly to reduced skin hydration. Whereas, if the portion of the outer cover 30 in the intermediate section 26 had such high levels of breathability, undesirable dampness and condensation on the outer cover 30 might occur as this is the region most likely to be saturated in use. Moreover, a high level of breathability of the outer cover 30 in the intermediate section 26 may allow the garment facing side of the absorbent to partially dry out but typically would not significantly reduce skin hydration after the absorbent is saturated. As a result, the zones of higher breathability in the waist sections provided by the extensible outer cover 30 of the diaper of the present invention can provide reduced skin hydration and improved skin health.

The extensible outer cover 30 of the different aspects of the present invention may also provide a lateral breathability gradient such that the side edges of the diaper have a greater level of breathability than the center of the diaper. For example, if the outer cover 30 is attached to other components of the diaper 20 such as the absorbent 34, the extension of the fasteners 40 in the lateral direction 50 extends the unattached portions of the outer cover 30 such as those laterally outward of the absorbent 34 a greater amount than the attached portions. Thus, the breathability of the unattached portions may be increased without resulting in a substantial increase in the breathability of the outer cover 30 overlying and attached to the absorbent 34. Thus, in use, the diaper 20 can also provide a lateral breathability gradient between center and side edges of the diaper. Such a lateral breathability gradient can provide reduced water vapor or humidity within the diaper 20 without excessive outer cover dampness and/or leakage since the portion of the outer cover 30 over the absorbent 34 can exhibit a lower level of breathability than the side margins of the diaper 20.

A suitable method of predicting such lateral and longitudinal breathability gradients during use is the Product Deformation Test described herein. In general, to determine the longitudinal breathability gradient, the breathability of the outer cover 30 located along the longitudinal centerline of the diaper between the fasteners 40 is determined and compared to the breathability of the outer cover 30 in the intermediate section 26 of the diaper 20 after the fasteners 40 on the diaper 20 are subjected to four cycles of a tensile force of 2000 gmf in the lateral direction 50, held at that extension for a period of 1 minute, and then allowed to relax, after a removal of the cyclic tensile force, for a period of at least 24 hours.

Desirably, the extensible outer cover 30 of the article of the present invention provides a longitudinal breathability gradient ratio between the regions of the outer cover 30 in the waist section 22 or 24 and the intermediate section 26 of the article of at least about 1.25, more desirably at least about 1.50, even more desirably at least about 1.75, and yet even more desirably at least about 2.00 when subjected to the Product Deformation Test. For example, the extensible outer cover 30 of the article of the present invention can provide a longitudinal breathability gradient ratio of from about 1.25 to about 30.00 for improved performance. Longitudinal breathability gradient ratios less than those set forth above may not provide the desired level of enhanced breathability or may result in excessive moisture on the outer cover in the intermediate section of the diaper in use.

In a particular embodiment, the extensible outer cover 30 defines a water vapor transmission rate of at least about 800 g/sq.m/24 hr., desirably at least about 1200 g/sq.m/24 hr, more desirably at least about 2000 g/sq.m/24 hr., and even more desirably at least about 3000 g/sq.m/24 hr. in the non-extended condition and a longitudinal breathability gradient ratio between the regions of the outer cover 30 in the waist section 22 or 24 and the intermediate section 26 of the article as set forth above when subjected to the Product Deformation Test for improved performance.

In general, to determine the lateral breathability gradient, a portion of the outer cover 30 centered about the intersection of the longitudinal centerline 54 of the article and a lateral line between the center of the fasteners 40 is removed and a portion of the outer cover 30 adjacent the fasteners along the laterally opposed side edges of the article and centered about the lateral line between the center of the fasteners 40 is also removed after the fasteners 40 on the diaper 20 are subjected to four cycles of a tensile force of 2000 gmf in the lateral direction 50, held at that extension for a period of 1 minute each and then allowed to relax, after a removal of the cyclic tensile force, for a period of at least about 24 hours.

Both portions are subjected to the Mocon Water Vapor Transmission Test set forth herein and the results are recorded. The lateral breathability gradient ratio of the outer cover 30 is then determined by dividing the breathability of the portion of the outer cover 30 taken adjacent the fasteners 40 by the portion of the outer cover taken from along the longitudinal centerline 54 of the article between the fasteners 40.

Desirably, the extensible outer cover 30 of the article of the present invention provides a lateral breathability gradient ratio between the regions of the outer cover 30 in the waist section 22 or 24 and the intermediate section 26 of the article of at least about 1.25, more desirably at least about 1.50, even more desirably at least about 1.75, and yet even more desirably at least about 2.00 when subjected to the Product Deformation Test. For example, the extensible outer cover 30 of the article of the present invention can provide a lateral breathability gradient ratio of from about 1.25 to about 10.00 for improved performance. Lateral breathability gradient ratios less than those set forth above may not provide the desired level of enhanced breathability or may result in excessive moisture on the outer cover located over the absorbent of the diaper in use.

In a particular embodiment, the extensible outer cover 30 defines a water vapor transmission rate of at least about 800 g/sq.m/24 hr., desirably at least about 1200 g/sq.m/24 hr, more desirably at least about 2000 g/sq.m/24 hr., and even more desirably at least about 3000 g/sq.m/24 hr. in the non-extended condition and provides a lateral breathability gradient ratio as set forth above when subjected to the Product Deformation Test for improved performance.

In the various configurations of the invention, the extensible outer cover 30 is also configured to be substantially impermeable to aqueous liquid. For example, the outer cover 30 can have a construction that is capable of supporting a selected hydrohead of water substantially without leakage therethrough. A suitable technique for determining the resistance of a material to liquid penetration is Federal Test Method Standard FTMS 191 Method 5514, 1978, or an equivalent thereof. Since the outer cover 30 is extensible, a layer of nylon net material having a thickness of about 0.1 mm may be needed to support the outer cover material for this test. The net material may be provided by nylon threads arranged in a hexagonal or honeycomb-like pattern with openings approximately 4 mm across. For example, the net material may be purchased from Wal-Mart Stores under the trade designation T-246. The net material is liquid pervious and does not significantly affect the hydrohead values obtained. The extensible outer cover 30 is sufficiently impermeable to liquid and semi-liquid materials to substantially prevent the undesired leakage of waste materials, such as urine and feces. For example, the extensible outer cover 30 can desirably support a hydrohead of at least about 45 centimeters (cm) substantially without leakage. The extensible outer cover 30 can alternatively support a hydrohead of at least about 55 cm, and optionally, can support a hydrohead of at least about 60 cm, or more, to provide improved benefits.

The extensible outer cover 30 can be composed of various materials that can provide the desired properties set forth herein. For example, the extensible outer cover 30 can be composed of a necked fabric, a creped fabric, a crimped fiber fabric, an extendable fiber fabric, a bonded-carded fabric, a micro-pleated fabric, polymer films or the like, as well as combinations thereof. The fabrics may be woven or nonwoven materials, such as spunbond fabrics. In a particular embodiment, the extensible outer cover 30 can be composed of an extensible laminate of two or more layers. For example, the extensible outer cover 30 may be a necked laminate formed from at least one neckable fabric laminated to at least one extendable film material wherein the necked laminate is extensible in at least one direction. The extensible outer cover 30 may otherwise be a laminate formed from at least one necked fabric laminated to at least one extendable film material. In such a configuration, the laminate need not be necked. For the purposes of the present description, the term "nonwoven web" means a web of fibrous material that is formed without the aid of a textile weaving or knitting process. The term "fabrics" is used to refer to all of the woven, knitted and nonwoven fibrous webs.

As used herein, the term "neck" or "neck stretch" interchangeably means that the fabric is drawn such that it is extended under conditions reducing its width or its transverse dimension by drawing and elongating to increase the length of the fabric. The controlled drawing may take place under cool temperatures, room temperature or greater temperatures and is limited to an increase in overall dimension in the direction being drawn up to the elongation required to break the fabric. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 entitled REVERSIBLY NECKED MATERIAL, by M. T. Morman which issued Oct. 23, 1990, the entire disclosure of which is hereby incorporated by reference, discloses a process for providing a reversibly necked nonwoven material which may include necking the material, then heating the necked material, followed by cooling.

As used herein, the term "neckable material or layer" means any material which can be necked such as a nonwoven, woven, or knitted material. As used herein, the term "necked material" refers to any material which has been drawn in at least one dimension, (e.g. lengthwise), reducing the transverse dimension, (e.g. width), such that when the drawing force is removed, the material can be pulled back to its original width. The necked material typically has a higher basis weight per unit area than the un-necked material. When the necked material is pulled back to its original un-necked width, it should have about the same basis weight as the un-necked material. This differs from stretching/orienting a material layer, during which the layer is thinned and the basis weight is permanently reduced.

Typically, such necked nonwoven fabric materials are capable of being necked up to about 80 percent. For example, the extensible outer cover 30 of the various aspects of the present invention may be provided by a material that has been necked from about 10 to about 80 percent, desirably from about 20 to about 60 percent, and more desirably from about 30 to about 50 percent for improved performance. For the purposes of the present disclosure, the term "percent necked" or "percent neckdown" refers to a ratio or percentage determined by measuring the difference between the pre-necked dimension and the necked dimension of a neckable material, and then dividing that difference by the pre-necked dimension of the neckable material and multiplying by 100 for percentage. The percentage of necking (percent neck) can be determined in accordance with the description in the above-mentioned U.S. Pat. No. 4,965,122.

In a particular embodiment, the extensible outer cover 30 is made from a necked laminate material to provide the desired levels of extensibility as well as liquid impermeability and vapor permeability. For example, the extensible outer cover 30 may be a necked laminate formed from sheet layers of at least one neckable fabric laminated to at least one film material wherein the necked laminate is extensible in at least one direction and does not appreciably retract. Desirably, both the neckable fabric and the film material are non-elastic materials for increased permanent set, reduced cost and improved manufacturing efficiency.

By the term "non-elastic", what is meant is that the sheet layers are made from polymers that are generally considered to be inelastic. In other words, use of such inelastic polymers to form the sheet layers would result in sheet layers that are not elastic. As used herein, the term "elastic" means any material which, upon application of a biasing force, is stretchable, that is, elongatable, at least about 60 percent (i.e., to a stretched, biased length which is at least about 160 percent of its relaxed unbiased length), and which will immediately recover at least 55 percent of its elongation upon release of the stretching, elongating force.

Suitable necked laminates that include at least one non-elastic neckable material laminated to at least one non-elastic film material are described in U.S. patent application Ser. No. 09/455,513 filed Dec. 6, 1999 and entitled "TRANSVERSELY EXTENSIBLE AND RETRACTABLE NECKED LAMINATE OF NON-ELASTIC SHEET LAYERS", the entire disclosure of which is hereby incorporated by reference.

In such a configuration, the non-elastic film layer can be made from either cast or blown film equipment, can be coextruded and can be embossed if so desired. The film layer may be made from any suitable non-elastic polymer composition and may include multiple layers. The non-elastic film layer can also be breathable. For example, the non-elastic film layer may contain such fillers as micropore developing fillers, e.g. calcium carbonate; opacifying agents, e.g. titanium dioxide; and antiblock additives, e.g. diatomaceous earth. Suitable polymers for the non-elastic film layer include but are not limited to non-elastic extrudable polymers such as polyolefin or a blend of polyolefins, nylon, polyester and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Alternative polymers for the film layer include those referred to as single site catalyzed polymers such as "metallocene" polymers produced according to a metallocene process and which have limited elastic properties. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Such metallocene polymers are available from Exxon Chemical Company of Baytown, Tex. under the trade name EXXPOL® for polypropylene based polymers and EXACT® for polyethylene based polymers and from Dow Chemical Company of Midland, Mich. under the name ENGAGE®. Preferably, the metallocene polymers are selected from copolymers of ethylene and 1-butene, copolymers of ethylene and 1-hexene, copolymers of ethylene and 1-octene and combinations thereof.

Suitable non-elastic neckable materials for such a configuration include nonwoven webs, woven materials and knitted materials such as those described in the above-mentioned U.S. Pat. No. 4,965,122. Nonwoven fabrics or webs have been formed from many processes, for example, bonded carded web processes, meltblowing processes and spunbonding processes. The non-elastic neckable material is preferably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof. Suitable fibers for forming the neckable material include natural and synthetic fibers as well as bicomponent, multi-component, and shaped polymer fibers. Many polyolefins are available for fiber production according to the present invention, for example, fiber forming polypropylenes include Exxon Chemical Company's Escorene® PD 3445 polypropylene and Himont Chemical Company's PF-304. Polyethylenes such as Dow Chemical's ASPUN® 6811A linear low density polyethylene, 2553 LLDPE and 25355 and 12350 high density polyethylene are also suitable polymers. The nonwoven web layer may be bonded to impart a discrete bond pattern with a prescribed bond surface area. If too much bond area is present on the neckable material, it will break before it necks. If there is not enough bond area, then the neckable material will pull apart. Typically, the percent bonding area useful in the present invention ranges from around 5 percent to around 40 percent of the area of the neckable material.

The non-elastic film layer may be laminated to the neckable material to form the laminate by conventional methods known in the art including adhesive bonding, point bonding, thermal point bonding, and sonic welding. The laminate is then necked by conventional necking processes that typically vary the surface speed of the web to draw or neck the laminate. Such necking provides striated rugosities in the film and/or laminate resulting in transverse extensibility and retractability to the necked laminate and more "cloth-like" aesthetics. It is known that stretching and orienting a filled film layer causes micropores to form in the film, but longitudinal striated rugosities do not typically form in the film layer when stretched. The film layer would instead become physically thinner and may narrow slightly. By necking the laminate, the non-elastic neckable material, which is attached to the non-elastic film layer, will neck and bring the non-elastic film layer with it, thereby forming the longitudinal striated rugosities in the film which allow the film layer to extend in the transverse direction.

Alternative necked laminate materials that could be used to provide the outer cover 30 of the different aspects of the present invention are described in U.S. patent application Ser. No. 09/460,490 filed Dec. 14, 1999 and entitled "BREATHABLE LAMINATE PERMANENTLY CONFORMABLE TO THE CONTOURS OF A WEARER", the entire disclosure of which is hereby incorporated by reference.

The bodyside liner 32, as representatively illustrated in FIG. 1, presents a body-facing surface that is compliant, soft-feeling, and non-irritating to the wearer's skin. Further, the bodyside liner 32 can be less hydrophilic than absorbent, body 34, and is sufficiently porous to be liquid permeable, permitting liquid to readily penetrate through its thickness to reach the absorbent composite. A suitable bodyside liner layer 32 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner layer 32 is typically employed to help isolate the wearer's skin from liquids held in the absorbent body 34.

Various woven and nonwoven fabrics can be used for bodyside liner 32. For example, the bodyside liner may be composed of a meltblown or spunbonded web of the desired fibers, and may also be a bonded-carded-web. Layers of different materials that may have different fiber deniers can also be used. The various fabrics can be composed of natural fibers, synthetic fibers or combinations thereof. The bodyside liner 32 may be composed of a substantially hydrophobic material, and the hydrophobic material may optionally be treated with a surfactant or otherwise processed to impart a desired level of wettability and hydrophilicity. In a particular embodiment of the invention, bodyside liner 32 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28 percent Triton X-102 surfactant. The surfactant can be applied by any conventional means, such as spraying, printing, brush coating or the like.

In particular embodiments, the bodyside liner 32 is desirably extensible such that it is capable of extending with the outer cover 30 to assist in providing the improved fastening, fit and containment discussed above. For example, the bodyside liner 32 can be composed of various extensible materials such as a necked fabric, a creped fabric, a micro-pleated fabric, perforated polymer films or the like, as well as combinations thereof. The fabrics may be woven or nonwoven materials, such as spunbond fabrics, that may be elastic or non-elastic. Examples of suitable manufacturing techniques and suitable necked nonwoven fabric materials for such an extensible bodyside liner 32 are described in U.S. Pat. No. 4,965,122 entitled REVERSIBLY NECKED MATERIAL, by M. T. Morman which issued Oct. 23, 1990.

Desirably, the bodyside liner 32 is made from non-elastic neckable materials for reduced cost and improved manufacturing efficiency. Suitable non-elastic neckable materials for such a configuration include nonwoven webs, woven materials and knitted materials. Such webs can include one or more fabric layers. Nonwoven fabrics or webs have been formed from many processes, for example, bonded carded web processes, meltblowing processes and spunbonding processes. The non-elastic neckable material is preferably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers, or filaments are used alone or in a mixture of two or more thereof. Suitable fibers for forming the neckable material include natural and synthetic fibers as well as bicomponent, multi-component, and shaped polymer fibers. Many polyolefins are available for fiber production according to the present invention, for example, fiber forming polypropylenes include Exxon Chemical Company's Escorene® PD 3445 polypropylene and Himont Chemical Company's PF-304. Polyethylenes such as Dow Chemical's ASPUN® 6811A linear low density polyethylene, 2553 LLDPE and 25355 and 12350 high density polyethylene are also suitable polymers. The nonwoven web layer may be bonded to impart a discrete bond pattern with a prescribed bond surface area. If too much bond area is present on the neckable material, it will break before it necks. If there is not enough bond area, then the neckable material will pull apart. Typically, the percent bonding area useful in the present invention ranges from around 5 percent to around 40 percent of the area of the neckable material.

For example, a particularly suitable extensible material for the bodyside liner 32 is a necked spunbond web of polypropylene fibers having a basis weight of from about 5 to about 30 gsm. Such a web may be necked up to about 80 percent.

The neckable material may be necked to form the extensible bodyside liner 32 by conventional necking processes that typically vary the surface speed of the web to draw or neck the material. Such necking will allow the material to extend and retract in the transverse direction. As discussed above, such necked nonwoven fabric materials typically are capable of being necked up to about 80 percent. For example, the extensible bodyside liner 32 of the various aspects of the present invention may be necked from about 10 to about 80 percent, desirably from about 20 to about 60 percent, and more desirably from about 30 to about 50 percent for improved performance.

In embodiments wherein the bodyside liner 32 is extensible, the bodyside liner can provide a substantially permanent deformation of at least about 10 percent, desirably at least about 20 percent, and more desirably at least about 30 percent when subjected to a tensile force of 100 gmf per inch (per 2.54 cm) of width of the test sample according to the Material Elongation and Deformation Tensile Test set forth herein. Substantially permanent deformations less than those set forth above may not provided the desired permanent deformation for improved fastening, containment and breathability discussed herein. In still other aspects, the bodyside liner 32 can provide a substantially permanent deformation of from about 10 to about 200 percent and desirably from about 20 to about 100 percent when subjected to the tensile force of 100 gmf per inch (per 2.54 cm) of width of the test sample according to the Material Elongation and Deformation Tensile Test set forth herein. The extensible bodyside liner 32 may also provide an elongation of at least about 20 percent, desirably at least about 25 percent and more desirably at least about 30 percent when subjected to a tensile force of 100 gmf per inch (per 2.54 cm) of width of the test sample according to the Material Elongation and Deformation Tensile Test set forth herein for improved performance.

Desirably, both the outer cover 30 and the bodyside liner 32 are extensible as set forth above for improved fit and performance. In configurations wherein both the outer cover 30 and the bodyside liner 32 are extensible, the diaper 20 can provide improved fit, resistance to leakage and breathability as the bodyside liner 32 does not restrict the ability of the outer cover 30 to maintain the substantially permanent deformation.

The bodyside liner 32 and outer cover 30 are connected or otherwise associated together in an operable manner. As used herein, the term "associated" encompasses configurations in which bodyside liner 32 is directly joined to the outer cover 30 by affixing the bodyside liner 32 directly to the outer cover 30, and configurations wherein the bodyside liner 32 is indirectly joined to the outer cover 30 by affixing the bodyside liner 32 to intermediate members which in turn are affixed to the outer cover 30. The bodyside liner 32 and the outer cover 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof.

For example, a uniform continuous layer of adhesive, a patterned layer of adhesive, a sprayed pattern of adhesive or an array of separate lines, swirls or spots of construction bonds may be used to affix the bodyside liner 32 to the outer cover 30. It should be readily appreciated that the above-described attachment mechanisms may also be employed to suitably interconnect, assemble and/or affix together the various other component parts of the articles that are described herein.

The absorbent body 34 provides an absorbent structure for holding and storing absorbed liquids and other waste materials, such as the shown absorbent pad composed of selected hydrophilic fibers and high-absorbency particles.

The absorbent body 34 may also be extensible or elastic. The absorbent body 34 is positioned and sandwiched between the bodyside liner 32 and outer cover 30 to form the diaper 20. The absorbent body 34 has a construction that is generally compressible, conformable, non-irritating to the wearer's skin, and capable of absorbing and retaining body exudates. It should be understood that, for purposes of this invention, the absorbent body may comprise a single, integral piece of material, or alternatively, may comprise a plurality of individual separate pieces of material which are operably assembled together.

Various types of wettable, hydrophilic fibrous material can be used to form the component parts of absorbent body 34. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact-angles greater than 90° are designated "nonwettable".

The absorbent body 34 can comprise a matrix of hydrophilic fibers, such as a web of cellulosic fluff, mixed with particles of high-absorbency material. In particular arrangements, the absorbent body 34 may comprise a mixture of superabsorbent hydrogel-forming particles or fibers and synthetic polymer meltblown fibers, or a mixture of superabsorbent particles or fibers with a fibrous coform material comprising a blend of natural fibers and/or synthetic polymer fibers.

The superabsorbent particles may be substantially homogeneously mixed with the hydrophilic fibers, or may be nonuniformly mixed. For example, the concentrations of superabsorbent particles may be arranged in a non-stepwise gradient through a substantial portion of the thickness (z-direction) of the absorbent body, with lower concentrations toward the bodyside of the absorbent body and relatively higher concentrations toward the garmentside of the absorbent body. Alternative distributions and methods of achieving such distributions are well known to this skilled in the art. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacryic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent composite include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the absorbent body 34 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 34. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

Optionally, a substantially hydrophilic tissue wrapsheet may be employed to help maintain the integrity of the fibrous structure of the absorbent body 34. The tissue wrapsheet is typically placed about the absorbent body over at least the two major facing surfaces thereof and composed of an absorbent cellulosic material, such as creped wadding or a high wet-strength tissue that may or may not be pleated. In one aspect of the invention, the tissue wrapsheet can be configured to provide a wicking layer which helps to rapidly distribute liquid over the mass of absorbent fibers comprising the absorbent body 34. The wrapsheet material on one side of the absorbent fibrous mass may be bonded to the wrapsheet located on the opposite side of the fibrous mass to effectively entrap the absorbent body 34.

With reference to FIGS. 1 and 2, each of the leg elastic members 36 can include a plurality of elastomeric strands.

Optionally, each leg elastic member may be a composite that includes at least one carrier layer (not shown), and the elastomeric strands can be operatively attached to the carrier layer. Various mechanisms, such as adhesive, thermal bonds, sonic bonds, or the like as well as combinations thereof, can be employed to provide the desired attachments between the elastomeric strands and the carrier layer. For example, each leg elastic member may be composed of a laminate of a plurality of elastomeric strands sandwiched and held between a pair of carrier layers. The carrier layers may desirably be composed of a woven or nonwoven fabric having a basis weight within the range of about 10–50 g/m², but may optionally be composed of a polymer film material. For example, the carrier layers may be composed of a polypropylene spunbond nonwoven fabric, and the pair of carrier layers may be adhesively bonded together with a suitable pattern of adhesive, such as a swirl-pattern of pressure-sensitive adhesive.

The leg elastic members 36 may have any of a multitude of configurations. For example, the width of the individual elastic members 36 may be varied from about 0.25 millimeters (0.01 inch) to about 25 millimeters (1.0 inch) or more. The elastic members may comprise a single strand of elastic material, or may comprise several parallel or nonparallel strands of elastic material, or may be applied in a rectilinear or curvilinear arrangement. Where the strands are non-parallel, two or more of the strands may intersect or otherwise interconnect within the elastic member. The elastic members may be affixed to the outer cover 30 and/or bodyside liner 32 of the diaper 20 in any of several ways that are known in the art. For example, the elastic members may be ultrasonically bonded, heat and pressure sealed using a variety of bonding patterns, or adhesively bonded to the diaper with sprayed or swirled patterns of adhesive.

In particular embodiments of the invention, the leg elastic members 36 may include a carrier sheet to which are attached a grouped set of elastics composed of a plurality of individual elastic strands. The elastic strands may intersect or be interconnected, or be entirely separated from each other. The carrier sheet may, for example, comprise a 0.002 inch thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 36 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper back waistband.

As discussed above, the forces exerted on the outer cover 30 when fastening the diaper 20 about the wearer's waist are typically localized in one or both of the front and rear waist sections 22 and 24 of the diaper 20 and generally do not substantially affect the intermediate section 26 of the diaper 20. As a result, the extension of the fasteners 40 upon the initial fastening about the wearer tends to cause the outer cover 30 in one or both of the front and rear waist sections 22 and 24 to extend and permanently deform. Such permanent deformation of the outer cover 30 in one or both of the waist sections results in an increase in the lateral distance between the leg elastics 36 toward such waist section. This increase in lateral distance between the leg elastics 36 in at least one of the waist sections 22 and 24 desirably occurs without a substantial increase in the lateral distance between the leg elastics 36 in the intermediate section 26 of the diaper 20 upon the fastening of the diaper 20 about the wearer. Such an increase in the curvature of the leg elastics 36 can result in configurations that were not practical with known manufacturing processes. The increase in curvature also allows the leg elastics to more closely conform to the wearer and can provide greater coverage over the hip regions of the wearer. Such improved fit and coverage can result in a reduced incidence of leakage. Moreover, diapers that are not extendable and, in particular, the leg elastics on such diapers can be very constrictive on the wearer's body during use undesirably leading to discomfort and potential skin irritation. Whereas, the extendability of the diaper of the different aspects of the present invention relieves such constriction and expands to improve fit and comfort.

Figure 6:
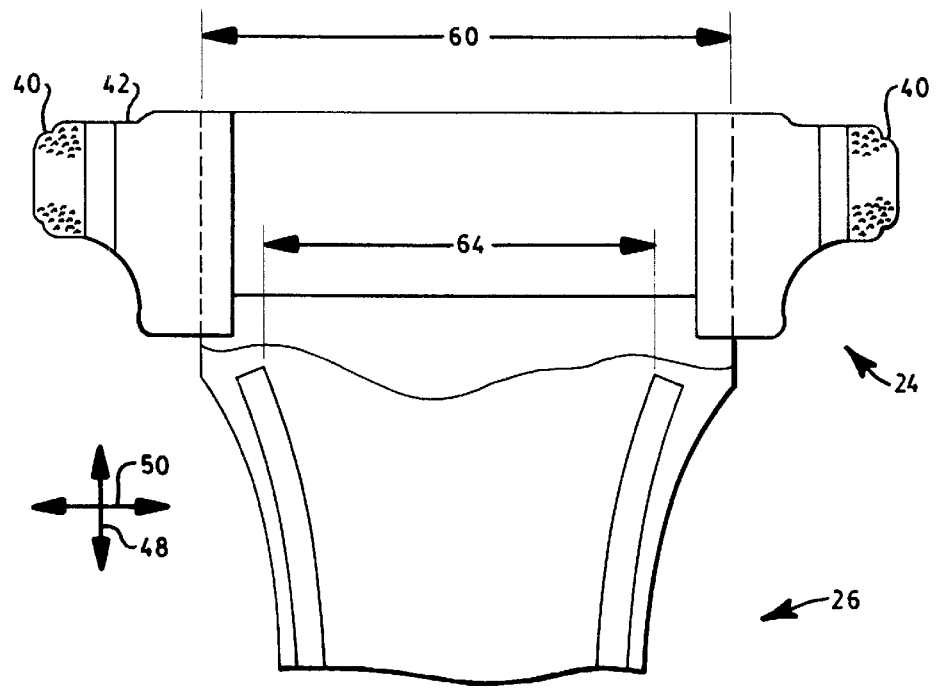
FIG. 6 representatively shows a partial top plan view of the inward surface of the article of FIG. 1 in a relaxed, non-extended configuration.
Figure 7:
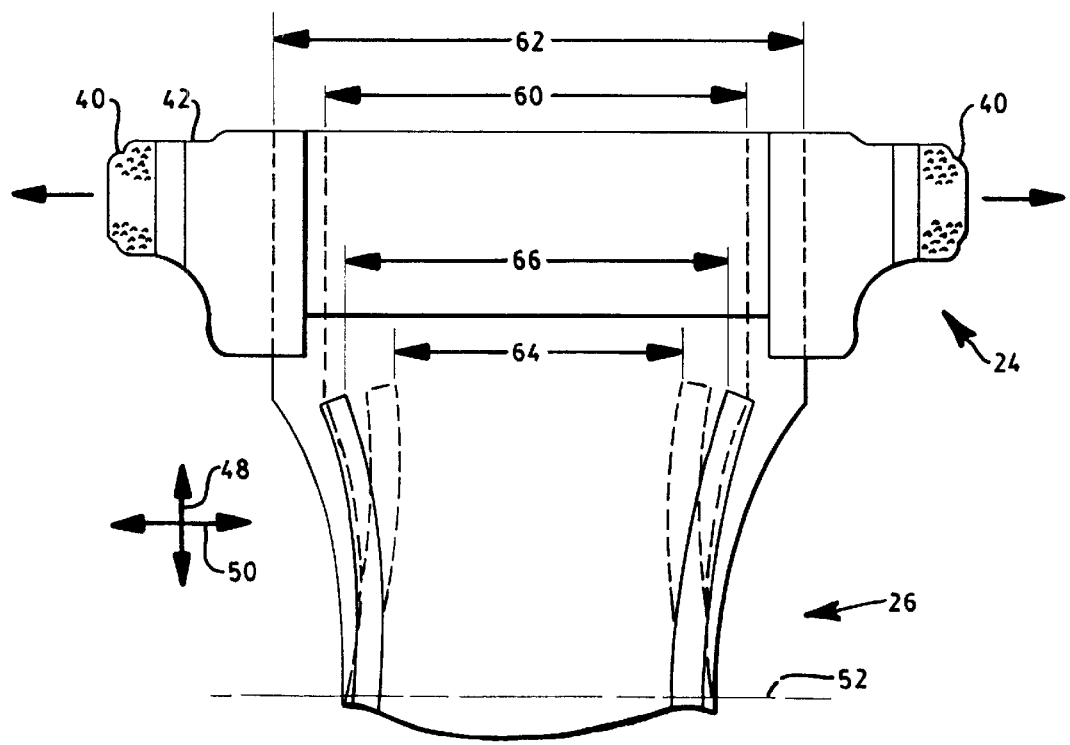
FIG. 7 representatively shows a partial top plan view of the inward surface of the article of FIG. 1 in a relaxed configuration after the fasteners in such article have been subjected to an extension force in the lateral direction thereby permanently extending the outer cover and leg elastics in the waist section of the article.

For example, as illustrated in FIGS. 6 and 7, the extensible outer cover 30 may define a non extended distance 60 between the fasteners 40 prior to use and an extended distance 62 after the fasteners 40 are extended in use to fasten the article about the waist of the wearer. As can be seen in the illustrated embodiment, the extension of the fasteners 40 in the lateral direction 50 extends and permanently deforms the outer cover 30 in the rear waist section 24 between the fasteners 40 but does not result in any substantial extension and permanent deformation of the outer cover 30 along the lateral centerline 52 of the diaper 20. As a result, in use, the leg elastics 36 of the diaper 20 can permanently deform with the outer cover 30 toward at least one of the waist sections 22 and 24 to provide enhanced curvature. For example, as representatively illustrated in FIGS. 6 and 7, the distance between the innermost edges of the leg elastics 56 in the lateral direction 50 may define a first dimension 64 before the fasteners 40 are extended and a second dimension 66 after the fasteners 40 have been extended upon the fastening of the diaper 20 on the wearer wherein the second dimension 66 is greater than the first dimension 64.

As a result, the diaper 20 of the different aspects of the present invention desirably provides increased curvature of the leg elastics in the waist sections 22 and 24 of the diaper 20 in use. A suitable method of predicting such levels of increased curvature of the leg elastics during use is the Product Deformation Test described herein. In general, the lateral width of the article in the non-extended condition is measured along a lateral line located about 40% of the distance between the centerline of the fasteners and the lateral centerline 52 of the article and recorded. The fasteners 40 on the diaper 20 are then subjected to four cycles of a tensile force of 2000 gmf in the lateral direction 50 each held at that extension for a period of 1 minute, and then allowed to relax, after a removal of the cyclic tensile force, for a period of at least 24 hours. The lateral width of the article in the same location is then measured and recorded and compared to the initial non-extended lateral width.

Desirably, the article of the present invention provides a permanent leg elastic deformation of at least about 3 percent, more desirably at least about 4 percent, even more desirably at least about 6 percent, and even more desirably at least about 10 percent when subjected to the Product Deformation Test. For example, the article of the present invention can provide a permanent leg elastic deformation of from about 3 to about 30 percent for improved performance. Permanent leg elastic deformations less than those set forth above may not provide the desired level of increased leg curvature and hip coverage in use.

As representatively illustrated in FIGS. 1 and 2, the absorbent article of the present invention also includes a pair of fasteners such as hook and loop fasteners 40. The fasteners 40 can be located at either or both of the front and rear waist sections 22 and 24. For example, in the representatively shown embodiment, each of the hook fasteners 40 are assembled and attached to extend from the side panels 42 that are attached to the laterally opposed side edges in the rear waist section 24.

In the various configurations of the invention, the fasteners 40 may include an adhesive, a cohesive, a complementary element of an interengaging mechanical fastening system, or the like, as well as combinations thereof. The mechanical fastener components can be provided by mechanical-type fasteners such as hooks, buckles, snaps, buttons and the like, which include cooperating and complementary, mechanically interlocking components. For example, as illustrated, the fasteners 40 may be a hook fastener of a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable.

Conventional hook and loop fastening systems are, for example, available under the VELCRO trademark. In a particular embodiment, the fasteners 40 may be a microhook material such as that distributed under the designation CS200 by 3M Company, a business having offices in St. Paul, Minn. Another suitable micro-hook material is distributed under the designation VELCRO CFM-29 1058, and is available from VELCRO U.S.A., Inc., a business having offices in Manchester, N.H.

The loop element may be provided directly by the outer cover 30 of the diaper 20 to provide a "fasten anywhere" mechanical fastening system for improved fastening. Alternatively, the diaper 20 may include one or more attachment panels (not illustrated) to which the fasteners 40 are configured to releasably engage. For example, when the fasteners 40 are hook fasteners located in the rear waist section 24 of the diaper 20 as illustrated, the diaper may include a corresponding attachment panel such as a complementary loop element on the outward facing surface in the front waist section 22. The attachment panels may be provided by a woven fabric, a nonwoven fabric, a knitted fabric, a perforated or apertured layer, and the like, as well as combinations thereof. For example, a suitable material for the attachment panel can be composed of a 2 bar, warp knit fabric of the type available from Guilford Mills, Inc., Greensboro, N.C. under the trade designation #34285, as well other of knit fabrics.

With reference to the representative configurations shown in FIGS. 1 and 2, the article can also include side panels 42. In particular arrangements, each side panel 42 extends laterally at the opposed, lateral ends of at least one waist section of the diaper 20, such as the representatively shown rear waist section 24, to provide terminal side sections of the article. In addition, each side panel 42 can substantially span from a laterally extending, terminal waist edge to approximately the location of its associated and corresponding leg opening section of the diaper. The diaper 20, for example, has a laterally opposed pair of leg openings provided by the curved margins of the side panels 42 in combination with the correspondingly adjacent, medial sections of the shown pair of longitudinally extending, side edges in the intermediate section 26 of the diaper 20.

In the various configurations of the invention, the side panels 42 may be integrally formed with a selected diaper component. For example, the side panels 42 can be integrally formed from the layer of material that provides the outer cover 30, or may be integrally formed from the material employed to provide the bodyside liner 32. In alternative configurations, the side panels 42 may be provided by one or more separately provided members that are connected and assembled to the outer cover 30, to the bodyside liner 32, in between the outer cover and bodyside liner, or in various fixedly attached combinations of such assemblies.

In particular configurations of the invention, each of the side panels 42 may be formed from a separately provided piece of material which is then suitably assembled and attached to the selected front and/or rear waist section of the article. For example, each side panel 42 may be attached to the rear waist section of the diaper 20, and can be operably attached to either or both of the outer cover 30 and bodyside liner 32 components of the article. The inboard, attachment zone region of each side panel can be overlapped and laminated with its corresponding, lateral end edge region of the waist section of the article. The side panels 42 extend laterally and are attached with suitable connecting means, such as adhesive bonding, thermal bonding, ultrasonic bonding, clips, staples, sewing or the like. Desirably, the side panels 42 extend laterally beyond the terminal side edges of the outer cover 30 and bodyside liner 32 at the corresponding waist section of the article.

The side panels 42 may be composed of a substantially non-elastomeric material, such as polymer films, woven fabrics, nonwoven fabrics or the like, as well as combinations thereof. In particular aspects of the invention, the side panels 42 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 50.

The different aspects of the present invention advantageously provide absorbent articles that have an extensible outer cover that provides improved fit and improved resistance to leakage. In particular, the extensible outer cover is capable of adjusting to the wearer's movements and changes in body dimensions for improved performance. In addition, the extensible outer cover on the articles provides improved breathability, greater softness, and more cloth-like properties. Moreover, in certain aspects, the present invention can also advantageously provide pant-like, prefastened, absorbent articles that are capable of being reliably pulled up or down over the hips of the wearer to assist in the toilet training of the wearer similar to conventional training pants.

Further, the different embodiments of the present invention, advantageously provide absorbent articles which exhibit a breathability gradient that can lead to substantially reduced levels of hydration of the wearer's skin and reduced clothing dampness when in use compared to conventional absorbent articles. The reduced levels of skin hydration promote drier, more comfortable skin and render the skin less susceptible to the growth of microorganisms. Thus, wearer's of absorbent articles made according to the present invention have reduced skin hydration that can lead to a reduction in the incidence of skin irritation and rash.

TEST PROCEDURES

Material Elongation and Deformation Tensile Test

A suitable technique for determining the amount of elongation, retractive force and or permanent deformation of a selected component or material can employ ASTM Standard Test Method D882 (Tensile Method for Tensile Properties of Thin Plastic Sheeting) dated December 1995, with the following particulars.

Equipment

1. Tensile tester capable of obtaining a peak load and equipped with an appropriate load cell. A suitable tensile testing system is a Sintech Tensile Tester, commercially available from MTS Sintech, Research Triangle Park, North Carolina, under the trade designation Model 1/G equipped with Sintech Testworks™ Version 3.10 Software.
2. Pneumatic-action grips having a 0.5 by 4 inch grip face.
3. Test facility having a temperature of 23±1° C., and a relative humidity of 50±2 percent.

The test sample width is perpendicular to the direction of the tensile force applied during the testing. With regard to the shown configurations, for example, the test sample "width" generally corresponds to the length-wise dimension of outer cover 30 along the longitudinal direction 48 of the article. The initial separation of the jaws of the tensile tester is 3 inches (76.2 mm) at a tensile force of about 1 gram force per inch of width of the test sample, and the moving jaw is moved at a constant rate of 127 mm/min. The moving jaw is stopped at an extension where the tensile force equals 100 grams force per inch of width of the test sample, held at that extension for a period of 2 minutes, and then returned back to its initial tensile force of about 1 gram force per inch of width of the test sample at a rate of 127 mm/min.

The percentage of elongation, extension or permanent deformation can be determined in accordance with the following formula:

$$100*(L-L_o)/(L_o);$$

where:

L=either a) extended length for elongation or extension or
b) post extended length for set or deformation, and
$L_o$=initial length.

Mocon Water Vapor Transmission Rate Test

A suitable technique for determining the WVTR (water vapor transmission rate) value of a material is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W model 100K manufactured by Mocon/Modem Controls, Inc, Minneapolis, Minn. A first test is made of the WVTR of the guard film and air gap between an evaporator assembly that generates 100 percent relative humidity. Water vapor diffuses through the air gap and the guard film and then mixes with a dry gas flow which is proportional to water vapor concentration. The electrical signal is routed to a computer for processing. The computer calculates the transmission rate of the air gap and guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$$TR^{-1}_{test\ material}=TR^{-1}_{test\ material,\ guardfilm,\ airgap}-TR^{-1}_{guardfilm,\ airgap}$$

Calculations:

WVTR: The calculation of the WVTR uses the formula:

$$WVTR=F\rho_{sat}(T)RH/A\rho_{sat}(T)(1-RH))$$

where:

F=The flow of water vapor in cc/min.,
$\rho_{sat}(T)$=The density of water in saturated air at temperature T,
RH=The relative humidity at specified locations in the cell,
A=The cross sectional area of the cell, and,
$\rho_{sat}(T)$=The saturation vapor pressure of water vapor at temperature T.

Product Deformation Test

A suitable technique for determining the deformation and the resulting increased breathability and leg elastic curvature of the article of the present invention when fastened about the wearer can employ the following test procedure. In general, a series of measurements are obtained on the article and, in particular, on the extensible outer cover of the article both before and after the fasteners 40 on the article are subjected to four cycles of a lateral tensile force of 2000 gmf in the lateral direction 50, each cycle being held at the extension where the tensile force reaches 2000 gmf for a period of 1 minute.

Sample Preparation

1. The product sample is clamped in a conventional vertical lightbox by hanging the product vertically with the rear waist section 24 of the product at the top of the lightbox and the outer cover 30 of the sample facing the viewer.
2. The top clamp is laterally centered on the end edge of the product.
3. A bottom clamp weighing 1000 grams is attached to the end edge of the product in the front waist section 22 and allowed to hang freely.

Figure 8:
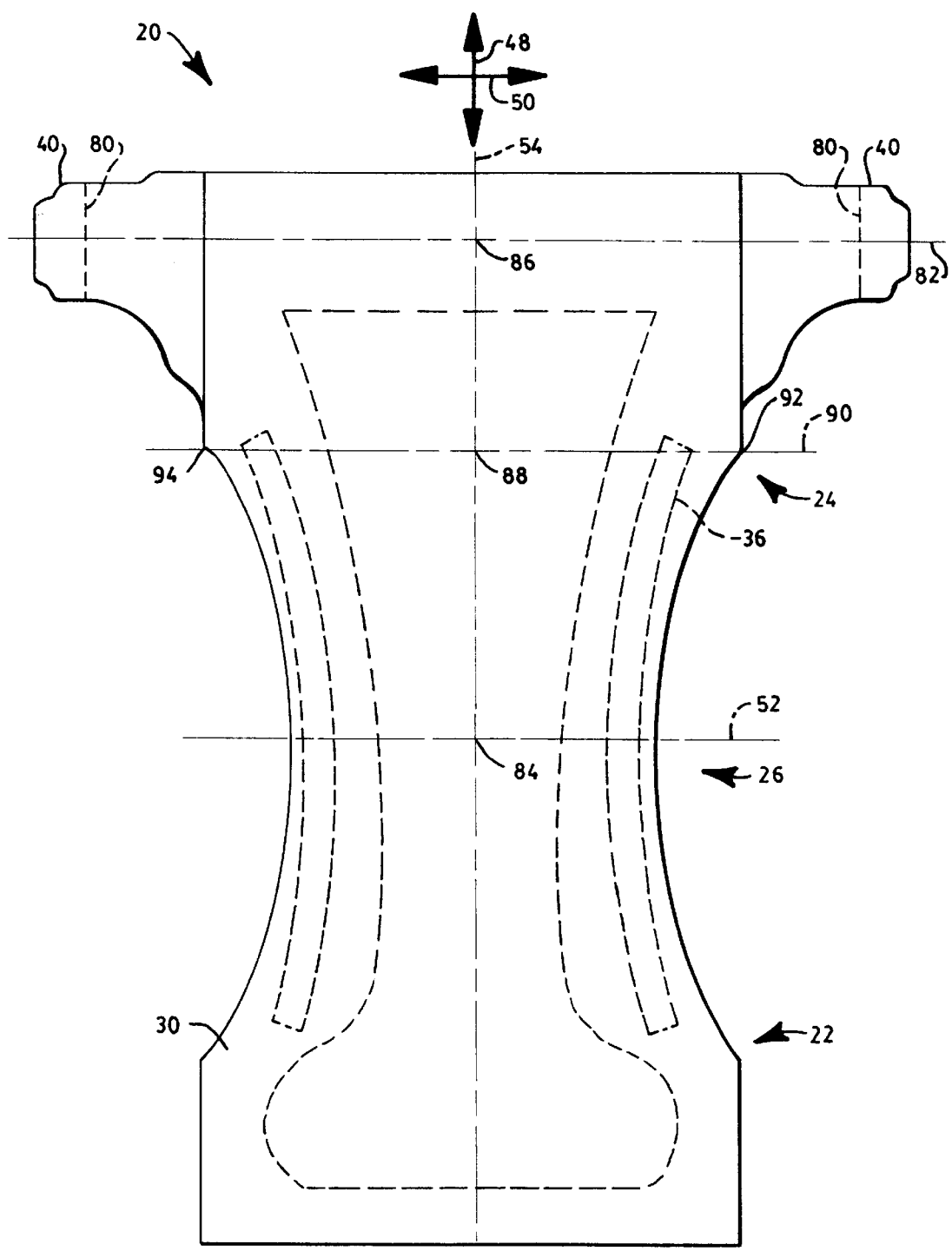
FIG. 8 representatively shows the article of FIG. 1 as prepared for the Product Deformation Test set forth herein.

4. With the product hanging, the following measurements and markings as illustrated in FIG. 8 are determined, recorded and marked on the outer cover 30 of the article.
5. Measure and mark the lateral centerline 52 of the product my measuring the total length of the product in the longitudinal direction 48, marking the centerpoint and constructing the lateral centerline 52 perpendicular to the longitudinal direction 48.
6. Measure and mark the longitudinal centerline 54 of the product my measuring the total width of the product in the lateral direction 50 along the lateral centerline 52, marking the centerpoint 84 and constructing the longitudinal centerline 54 perpendicular to the lateral centerline 52.
7. Measure the inboard longitudinal edge 80 of the fasteners 40, mark the center of the inboard edge 80 of the fasteners, and draw a line between the centers to provide the centerline 82 of the fasteners 40 which intersects the longitudinal centerline 54 at point 86.
8. Measure the distance between points 84 and 86 along the longitudinal centerline 54, and mark the position 88 at a location from point 84 along the longitudinal centerline 54 a distance equal to 40% of the distance between points 84 and 86 along the longitudinal centerline 54.
9. Construct a lateral line 90 through point 88 and perpendicular to the longitudinal centerline 54.
10. The points at which the lateral line 90 intersects the side edges of the product are marked 92 and 94, respectively, and the distance between 92 and 94 is measured and recorded.

Equipment
1. Tensile tester capable of obtaining a peak load and equipped with an appropriate load cell. A suitable tensile testing system is a Sintech Tensile Tester, commercially available from MTS Sintech, Research Triangle Park, North Carolina, under the trade designation Model 1/G equipped with Sintech Testworks™ Version 3.10 Software.
2. Pneumatic-action grips having 0.5 by 4 inch grip faces.
3. Test facility having a temperature of 23±1° C., and a relative humidity of 50±2 percent.

Test Procedure
1. A product to be tested is conditioned in the test facility for at least 4 hours prior to testing.
2. The load cell is calibrated and the software loaded.
3. The grips are installed on the tensile tester with the jaws closed.
4. One of the fasteners 40 of the article is inserted into the upper jaw such that the edge of the grip face is flush with the inboard edge 80 of the fastener material.
5. Tare the weight of the clamp and the product out.
6. Align the lower jaw with the inboard edge 80 of the opposite fastener 40 and close it.
7. Adjust the initial tensile load on the product to be 5 gmf by adjusting the upper jaw position.
8. Activate the upper jaw so that it travels away from the lower jaw at a constant speed of 127 mm/min.
9. The movement of the upper jaw stops when the tensile load on the product is 2000 gmf.
10. Hold the extension for a period of 1 minute before returning the upper jaw to its initial position at a constant speed of 127 mm/min.
11. The upper jaw holds at the initial position for a period of 1 minute.
12. Repeat steps 8–11 three additional times.
13. Remove the product from the tester.

Leg Elastic Deformation

After removal from the tester, the product is allowed to relax for a period of at least 24 hours. The product is then placed on the lightbox following the sample preparation procedures set forth above. The post extended distance between points 92 and 94 is measured. The percent permanent leg elastic deformation value is then determined by subtracting the initial distance between points 92 and 94 from the post extended distance, then dividing by the initial distance and multiplying by 100 in accordance with the following formula:

$$100*(D-D_o)/(D_o);$$

where:
D=post extended distance, and
$D_o$=initial distance

Breathability Enhancement

After removal from the tester, the product allowed to relax for a period of at least 24 hours.

To determine the longitudinal breathability gradient ratio, a portion of the outer cover material centered about point 86 (i.e. the intersection of the longitudinal centerline 54 of the article and a lateral line 82 between the center of the fasteners 40) is removed. In addition, a portion of the outer cover material centered about point 84 (i.e. the intersection of the longitudinal 54 and lateral centerlines 52 in the intermediate section 26 of the article) is also removed. Both portions are subjected to the Mocon Water Vapor Transmission Test set forth herein and the results are recorded. The longitudinal breathability gradient ratio of the outer cover 30 is then determined by dividing the breathability of the portion of the outer cover 30 taken between the fasteners by the portion of the outer cover taken from the intermediate section 26 of the article.

To determine the lateral breathability gradient ratio, a portion of the outer cover material centered about point 86 (i.e. the intersection of the longitudinal centerline 54 of the article and a lateral line 82 between the center of the fasteners 40) is removed. In addition, a portion of the outer cover material nearest the fasteners along the laterally opposed side edges of the article and centered about the lateral line 82 between the center of the fasteners 40 is also removed. Both portions are subjected to the Mocon Water Vapor Transmission Test set forth herein and the results are recorded. The lateral breathability gradient ratio of the outer cover 30 is then determined by dividing the breathability of the portion of the outer cover 30 taken adjacent the fasteners by the portion of the outer cover taken from along the longitudinal centerline of the article between the fasteners.

EXAMPLES

The following examples are presented to provide a more detailed understanding of the invention. The examples are representative, and are not intended to limit the scope of the invention Example 1

A necked laminate suitable for the extensible outer cover of the present invention was prepared from a non-elastic film layer and a non-elastic nonwoven web layer. A 1.5 mil layer of blown film made of 48 percent by weight (25 volume percent) SUPERCOAT calcium carbonate as manufactured by English China Clay America, Inc. of Sylacauga, Ala., 47 percent by weight (68 volume percent) linear low density polyethylene (LLDPE) available under the trade designation DOWLEX NG3347A as manufactured by the Dow Chemical Company ("Dow"), 5 percent by weight (7 volume percent) low density polyethylene (LDPE) available under the trade designation 6401 as manufactured by Dow, and 2000 ppm antioxidant stabilizer available under the trade designation B900 as manufactured by Ciba Specialties Company of Tarrytown, N.Y. The film layer, made of the composition as described above, was pre-made and wound onto a roll. The film layer was then unwound from a film unwind unit into a conventional machine direction orienter, such as that manufactured by the Marshall and Williams Company, where it was partially stretched in the machine direction to form a partially stretched, breathable film layer.

Likewise, a 0.4 osy basis weight standard polypropylene spunbond having a wireweave bond pattern, such as that available from the Kimberly-Clark Corporation of Dallas, Tex., was unwound and an adhesive of 3 gsm weight (at the application point) available as H2525A from Ato-Findley of Wauwatosa, Wis. was applied to one surface of the nonwoven web layer using an air assisted spraying device such as a meltblown device. Such devices are generally described in, for example, commonly assigned U.S. Pat. No. 4,949,668 to Heindel et al.; U.S. Pat. No. 4,983,109 to Miller et al., assigned to Nordson Corporation; and U.S. Pat. No. 5,728,219 to Allen et al., assigned to J&M Laboratories, Inc.

The adhesive side of the nonwoven web layer was then laminated to the partially stretched film layer using laminating rollers at a pressure of 30 pli (5.4 kg/linear cm) of a smooth resilient (rubber coated) anvil roll on one side and a smooth, unheated steel roll. The laminate was then stretched in the longitudinal dimension and necked in the transverse dimension by passing it through a stretch nip at a greater speed than the speed of the laminating rollers. The necking draw caused contraction (necking) of the laminate in the transverse direction. The laminate was necked 33 percent (i.e. to about two thirds of the laminates pre-stretched width).

Samples of the outer cover material described in Example 1 were tested and compared to samples of outer cover material from HUGGIES Ultratrim diapers commercially available from Kimberly-Clark Corporation and PAMPERS Baby Dry diapers commercially available from The Procter and Gamble Company. The outer cover material from the diaper samples was obtained by measuring the length of the diaper in the longitudinal direction 48 (FIG. 1) and obtaining a sample from a location offset from the waist edge of the diaper in the rear waist section 24 a distance equal to 25 percent of the diaper length.

Six samples of the outer cover materials were then subjected to the Material Elongation and Deformation Tensile Test set forth above. The results of such test are set forth in Table 1 below. The initial distance between the jaws of the tensile tester for each sample was 76.2 mm at an initial force of 1 gmf per inch of width.

TABLE 1

| Material | Extended Length @ 100 gmf per inch (mm) | Postextended Length @ 1 gmf per inch (mm) | Percent Elongation | Percent Permanent Deformation |
| --- | --- | --- | --- | --- |
| Example 1 | 102.7 | 97.0 | 34.8% | 27.3% |
| HUGGIES | 77.2 | 76.7 | 1.4% | 0.6% |
| PAMPERS | 96.0 | 87.8 | 26.0% | 15.3% |

The results show that the outer cover material of Example 1 exhibits greater elongations and deformation than the outer cover material from conventional diapers. The combination of high elongation and high deformation or set of the outer cover material of Example 1 can provide a diaper that "gives" when cross directional forces are exerted on the outer cover material during fastening and wear. Thus, such an outer cover can more readily conform and adjust to the changing body dimensions of the wearer as they move for improved fit and reduction in leakage. Moreover, such an outer cover can also readily expand as the absorbent body in the diaper receives repeated insults and expands to provide more void volume in the diaper for improved containment.

Example 2

Necked laminates suitable for the extensible outer cover of the present invention were prepared from two different film layers (Material A and Material B) each individually laminated to a non-elastic nonwoven web layer.

Material A included a 1.8 mil layer of blown film made of 52% by weight calcium carbonate, and 48% by weight of a polymer combination. The polymer combination included 41.7% by weight DOW EG-8200, single-site catalyzed very low density polyethylene having a density of 0.87 grams per cubic centimeter and an octene comonomer available from Dow Chemical Company ("Dow"). The polymer combination also included 58.3% by weight DOWLEX 2517, a Ziegler-Natta catalyzed linear low density polyethylene (LLDPE) having a density of 0.917 grams per cubic centimeter available from Dow.

Material B included a 1.8 mil layer of blown film made of 52 percent by weight calcium carbonate and 48 percent by weight of a polymer combination. The polymer combination included 20.3 percent by weight DOW EG-8200 and 79.7 percent by weight DOWLEX 2517 available from Dow.

The film layers, made of the composition as described above, were pre-made and wound onto a roll. The film layers were then unwound from a film unwind unit into a conventional machine direction orienter, such as that manufactured by the Marshall and Williams Company, where they were stretched in the machine direction to four times their original length to form a stretched, breathable film layer. A 21 gsm basis weight, 33 percent necked, polypropylene spunbond material was unwound and an adhesive of 3 gsm weight (at the application point) available as H2525A from Ato-Findley of Wauwatosa, Wis. was applied to one surface of the nonwoven web layer using an air assisted spraying device such as a meltblown device. The adhesive side of the nonwoven web layer was then laminated to each of the stretched film layers using laminating rollers at a pressure of 30 pli (5.4 kg/linear cm) of a smooth resilient (rubber coated) anvil roll on one side and a smooth, unheated steel roll.

Material A and Material B were then subjected to the Mocon Water Vapor Transmission Rate Test set forth above both in a non-extended condition and while being held at an extension of 25 percent in the cross machine direction. The results are set forth below in Table 2.

TABLE 2

| Laminate | WVTR @ 0% Extension | WVTR @ 25% Extension | Percent Increase |
|---|---|---|---|
| Material A | 800 | 7000 | 675% |
| Material B | 19000 | 37000 | 95% |

The results show that the outer cover materials of Example 2 exhibit substantial increases in breathability when subjected to fairly low extensions. As a result, articles incorporating such materials should exhibit enhanced breathability in use for improved performance.

Examples 3–6

Examples of diapers of the present invention including the outer cover materials described in Examples 1 and 2 were tested to determine the leg elastic deformation and compared to Step 4 sized HUGGIES Ultratrim diapers commercially available from Kimberly-Clark Corporation and Extra Large PAMPERS Baby Dry diapers commercially available from The Procter and Gamble Company.

The Example 1 and 2 diapers provided a "size 4" diaper for an infant weighting between 22 and 37 pounds. The diapers had the configurations and shapes illustrated in FIGS. 1 and 2.

The outer cover 30 included the extensible materials set forth in Examples 1 and 2. The bodyside liner 32 included a standard polypropylene spunbond material having a basis weight of 0.6 osy that was neck stretched 45 percent. The absorbent body 34 included a pleated cellulose tissue wrap sheet that was overlaid onto an absorbent core comprising a mixture of 40 percent cellulosic, woodpulp fluff and 60% superabsorbent polymer (FAVOR SXM-880 from Stockhausen). A layer of surge material 44 was placed between the absorbent 34 and the bodyside liner 32. The surge layer had a basis weight of about 3.55 osy. The surge layer measured 51 mm in the lateral direction and 178 mm in the longitudinal direction. Another layer of necked SMS material having a basis weight of 0.8 osy was placed between the absorbent 34 and the outer cover 30. The SMS layer measured 51 mm in the lateral direction and 388 mm in the longitudinal direction.

In the machine made diapers, the outer cover 30 was adhesively attached to the necked SMS material and the tissue wrap sheet on the garment facing surface of the absorbent body 34 using pressure sensitive, hot melt adhesive at an add-on rate of about 3 gsm. The adhesive was deposited in the form of adhesive swirls across the entire mating surface. The layers are bonded together by passing the composite through a nip while the adhesive is still warm enough to effect bonding.

In the hand made diapers, the outer cover 30 was adhesively attached to the SMS material and the tissue wrap sheet on the garment facing surface of the absorbent body 34 using pressure sensitive, hot melt adhesive at an add-on rate of about 5 gsm. In the rear waist section, the adhesive was deposited in the form of a continuous band on and around the perimeter of the SMS material in a picture frame like pattern.

The diaper also had a pair of leg elastics 36. Each leg elastic member 36 included three, 620 dtx (decitex) elastomeric strands 98 composed of LYCRA XA SPANDEX elastomer.

The elastomeric strands were elongated to 250% elongation and adhesively laminated between two layers of 0.4 osy polypropylene spunbond facing layers with a FINDLEY H2525A adhesive. The leg elastic members were stretched-to-stop, and adhesively laminated to the side marginal edges of the outer cover 30. Accordingly, the laterally opposed pair of leg elastic members 36 created a gathered element at each leg opening of the diaper.

Six samples of all diapers were then subjected to the Product Deformation Test set forth above. The results of such test are set forth in Table 3 below.

TABLE 3

| Diaper | Percent Permanent Leg Elastic Deformation |
|---|---|
| Example 3 - Hand made with Ex. 1 material | 3.8% |
| Example 4 - Machine made with Ex. 1 material | 17.3% |
| Example 5 - Hand made with Ex. 2 Material A | 5.6% |
| Example 6 - Hand made with Ex. 2 Material B | 6.2% |
| HUGGIES | 0.5% |
| PAMPERS | 1.4% |

The results show that the diaper of Examples 3–6 exhibit greater leg elastic deformations than the conventional diapers. The combination of high elongation and high deformation or set of the diaper of Example 2 can provide a diaper that "gives" when cross directional forces are exerted on the diaper during fastening and wear. Thus, such a diaper can more readily conform and adjust to the changing body dimensions of the wearer as they move for improved fit and reduction in leakage. Moreover, the leg elastics on such a diaper can exhibit permanent lateral extension and enhanced curvature in use to provide greater coverage without requiring difficult manufacturing processes. Further, the outer cover on such a diaper also readily expand as the absorbent body in the diaper receives repeated insults and expands to provide more void volume in the diaper for improved containment.

One of the reasons that the Example 3 diaper of the present invention exhibited such high extensions and deformations compared to the tested commercial diapers when subjected to the Product Deformation Test set forth above is that it includes a bodyside liner material that is extensible. To illustrate such differences, the bodyside liner was removed from Example 3 diapers and PAMPERS Baby Dry diapers and subjected to the Material Elongation and Deformation Tensile Test set forth above. The results of such test are set forth in Table 4 below. The distance between the jaws of the tensile tester for each sample was 76.2 mm at an initial force of 1 gmf per inch of width.

TABLE 4

| Material | Extented Length @ 100 gmf per inch (mm) | PostExtended Length @ 1 gmf per inch (mm) | Percent Elongation | Percent Permanent Deformation |
|---|---|---|---|---|
| Example 3 liner | 121.1 | 102.8 | 58.9% | 34.9% |
| PAMPERS liner | 87.3 | 82.8 | 14.5% | 8.6% |

The results show that the bodyside liner from the diaper of Example 3 exhibits significantly greater elongations and deformation than the bodyside liner removed from the conventional diapers that were tested. Using such an extensible bodyside liner allows the extensible outer cover to more freely extend and permanently deform. As discussed above, the combination of high elongation and high deformation or set of both the bodyside liner and the outer cover of the Example 3 diapers can provide a diaper that "gives" when cross directional forces are exerted on the diaper during fastening and wear for improved performance.

Examples 7–10

Examples of diapers of the present invention made according to Examples 3–6 above were tested and compared to Step 4 sized HUGGIES Ultratrim diapers commercially available from Kimberly-Clark Corporation to determine the longitudinal breathability gradient ratio. The PAMPERS Baby Dry diapers commercially available from The Procter and Gamble Company identified in Examples 3–6 were not included as their outer cover was not breathable in the intermediate or crotch section (i.e. exhibited a WVTR in the intermediate section of 0). Six samples of all diapers were subjected to the Product Deformation Test set forth above to determine the longitudinal breathability gradient ratio. The results of such test are set forth in Table 5 below.

TABLE 5

| Diaper | Longitudinal Breathability Gradient |
|---|---|
| Example 7 - Hand made with Ex. 1 material | 2.34 |
| Example 8 - Machine made with Ex. 1 material | 1.00 |
| Example 9 - Hand made with Ex. 2 Material A | 4.25 |
| Example 10 - Hand made with Ex. 2 Material B | 2.34 |
| HUGGIES | 0.95 |

The results show that the diaper of Examples 7, 9 and 10 exhibit greater longitudinal breathability gradient ratios and deformation than the conventional diapers. The combination of high elongation and high deformation or set of the diapers of the Examples can provide a diaper that has enhanced breathability in use that can lead to reduced skin hydration and improved skin health.

With regards to Example 8, it is believed that such material did not exhibit an increased longitudinal breathability gradient ratio since the composite outer cover was not extended a sufficient amount in the test to extend the film layer of the material enough to cause permanent set in the film and the resulting increase in breathability in the film.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said absorbent article comprising:
   a) a substantially liquid-impermeable extensible outer cover;
   b) a liquid permeable extensible bodyside liner; and
   c) an absorbent body located between said extensible outer cover and said extensible bodyside liner;
   wherein said extensible outer cover and said extensible bodyside liner are configured to provide a substantially permanent deformation of at least about 10 percent when subjected to a tensile force of 100 gmf per inch (per 2.54 cm) of width according to a Material Elongation and Deformation Tensile Test set forth herein.

2. The disposable absorbent article of claim 1 wherein said substantially permanent deformation of said extensible outer cover is at least about 15 percent.

3. The disposable absorbent article of claim 1 wherein said substantially permanent deformation of said extensible outer cover is at least about 17 percent.

4. The disposable absorbent article of claim 1 wherein said extensible outer cover is also configured to provide an elongation of at least about 20 percent when subjected to said tensile force of 100 gmf per inch (per 2.54 cm) of width.

5. The disposable absorbent article of claim 4 wherein said elongation of said extensible outer cover is at least about 30 percent.

6. The disposable absorbent article of claim 1 wherein said extensible bodyside liner is also configured to provide an elongation of at least about 20 percent when subjected to said tensile force of 100 gmf per inch (per 2.54 cm) of width.

7. The disposable absorbent article of claim 1 wherein said substantially permanent deformation of said extensible bodyside liner is at least about 20 percent.

8. The disposable absorbent article of claim 1 wherein said extensible outer cover and said extensible bodyside liner are configured to provide an elongation of at least about 20 percent and a substantially permanent deformation of at least about 10 percent when subjected to said tensile force of 100 gmf per inch (per 2.54 cm) of width according to said Material Elongation and Deformation Tensile Test set forth herein.

9. The disposable absorbent article of claim 1 wherein said extensible outer cover comprises a necked laminate which includes at least one layer of a non-elastic neckable material and at least one layer of a non-elastic film.

10. A disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said absorbent article comprising:
   a) a substantially liquid-impermeable, extensible outer cover that defines a water vapor transmission rate of at least about 800 g/m$^2$/24 hr when subjected to a Mocon Water Vapor Transmission Test as set forth herein;
   b) a liquid permeable extensible bodyside liner; and
   c) an absorbent body located between said extensible outer cover and said extensible bodyside liner;
   wherein said extensible outer cover and said extensible bodyside liner are configured to provide a substantially permanent deformation of at least about 10 percent when subjected to a tensile force of 100 gmf per inch (per 2.54 cm) of width according to a Material Elongation and Deformation Tensile Test set forth herein.

11. The disposable absorbent article of claim 10 wherein said substantially permanent deformation of said extensible outer cover and said extensible bodyside liner is at least about 20 percent.

12. The disposable absorbent article of claim 10 wherein said substantially permanent deformation of said extensible outer cover is at least about 17 percent.

13. The disposable absorbent article of claim 10 wherein said extensible outer cover is also configured to provide an elongation of at least about 20 percent when subjected to said tensile force of 100 gmf per inch (per 2.54 cm) of width.

14. The disposable absorbent article of claim 13 wherein said elongation of said extensible outer cover is at least about 30 percent.

15. The disposable absorbent article of claim 10 wherein said extensible bodyside liner is also configured to provide an elongation of at least about 20 percent when subjected to said tensile force of 100 gmf per inch (per 2.54 cm) of width.

16. The disposable absorbent article of claim 15 wherein said elongation of said extensible bodyside liner is at least about 25 percent.

17. The disposable absorbent article of claim 10 wherein said water vapor transmission rate of said extensible outer cover is at least about 1200 g/m$^2$/24 hr.

18. The disposable absorbent article of claim 10 wherein said water vapor transmission rate of said extensible outer cover is at least about 2000 g/m$^2$/24 hr.

19. The disposable absorbent article of claim 10 wherein said extensible outer cover comprises a necked laminate which includes at least one layer of a non-elastic neckable material and at least one layer of a non-elastic film.

20. A pant-like, prefastened, disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said pant-like absorbent article comprising:
a) a substantially liquid-impermeable extensible outer cover;
b) a liquid permeable extensible bodyside liner;
c) an absorbent body located between said extensible outer cover and said extensible bodyside liner; and
d) a pair of fasteners refastenably attaching said laterally opposed side edges in said front waist section to said laterally opposed side edges in said rear waist section to provide said pant-like, prefastened absorbent article prior to packaging;
wherein said extensible outer cover and said extensible bodyside liner are configured to provide a substantially permanent deformation of at least about 10 percent when subjected to a tensile force of 100 gmf per inch (per 2.54 cm) of width according to a Material Elongation and Deformation Tensile Test set forth herein.

21. The pant-like, prefastened, disposable absorbent article of claim 20 wherein said substantially permanent deformation of said extensible outer cover and said extensible bodyside liner is at least about 20 percent.

22. The pant-like, prefastened, disposable absorbent article of claim 20 wherein said substantially permanent deformation of said extensible outer cover is at least about 17 percent.

23. The pant-like, prefastened, disposable absorbent article of claim 20 wherein said extensible outer cover is also configured to provide an elongation of at least about 20 percent when subjected to said tensile force of 100 gmf per inch (per 2.54 cm) of width.

24. The pant-like, prefastened, disposable absorbent article of claim 23 wherein said elongation of said extensible outer cover is at least about 30 percent.

25. The pant-like, prefastened, disposable absorbent article of claim 20 wherein said extensible bodyside liner is also configured to provide an elongation of at least about 20 percent when subjected to said tensile force of 100 gmf per inch (per 2.54 cm) of width.

26. The pant-like, prefastened, disposable absorbent article of claim 25 wherein said elongation of said extensible bodyside liner is at least about 25 percent.

27. The pant-like, prefastened, disposable absorbent article of claim 20 wherein said extensible outer cover and said extensible bodyside liner are configured to provide an elongation of at least about 20 percent and a substantially permanent deformation of at least about 10 percent when subjected to said tensile force of 100 gmf per inch (per 2.54 cm) of width according to said Material Elongation and Deformation Tensile Test set forth herein.

28. The pant-like, prefastened, disposable absorbent article of claim 20 wherein said extensible outer cover comprises a necked laminate which includes at least one layer of a non-elastic neckable material and at least one layer of a non-elastic film.

29. A disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said absorbent article comprising:
a) a substantially liquid-impermeable extensible outer cover, wherein the extensible outer cover is a necked laminate including at least one neckable nonwoven material;
b) a liquid permeable extensible bodyside liner, wherein the extensible bodyside liner includes a necked nonwoven material; and
c) an absorbent body located between said extensible outer cover and said extensible bodyside liner;
wherein said extensible outer cover and said extensible bodyside liner are configured to provide a substantially permanent deformation of at least about 10 percent when subjected to a tensile force of 100 gmf per inch (per 2.54 cm) of width according to a Material Elongation and Deformation Tensile Test set forth herein.

30. A disposable absorbent article which defines a front waist section, a rear waist section, an intermediate section which extends between and connects said waist sections, a pair of laterally opposed side edges, a pair of longitudinally opposed waist edges, a longitudinal direction and a lateral direction, said absorbent article comprising:
a) a substantially liquid-impermeable extensible outer cover, wherein the extensible outer cover is a laminate including at least one necked nonwoven material;
b) a liquid permeable extensible bodyside liner wherein the extensible bodyside liner includes a necked nonwoven material; and
c) an absorbent body located between said extensible outer cover and said extensible bodyside liner;
wherein said extensible outer cover and said extensible bodyside liner are configured to provide a substantially permanent deformation of at least about 10 percent when subjected to a tensile force of 100 gmf per inch (per 2.54 cm) of width according to a Material Elongation and Deformation Tensile Test set forth herein.

* * * * *

UNITED STATES PATENT AND TRADEMARK OFFICE
CERTIFICATE OF CORRECTION

PATENT NO.   : 6,552,245 B1
DATED        : April 22, 2003
INVENTOR(S)  : Roessler et al.

It is certified that error appears in the above-identified patent and that said Letters Patent is hereby corrected as shown below:

Column 26,
Line 33, replace "WVTR=F$\rho_{sat}$(T)RH/A$\rho_{sat}$(T)(1-RH))" with
-- WVTR=F$\rho_{sat}$(T)RH/A$p_{sat}$(T)(1-RH)) --
Line 43, replace "$\rho_{sat}$(T)" with -- $p_{sat}$(T) --

Signed and Sealed this

Twenty-sixth Day of October, 2004

JON W. DUDAS
*Director of the United States Patent and Trademark Office*